US012752245B2

(12) United States Patent
Sabev et al.

(10) Patent No.: US 12,752,245 B2
(45) Date of Patent: Oct. 6, 2026

(54) MICROWAVE NETWORKS, WAVEGUIDES, MIXING CARTS, METHODS OF SUPPLYING GAS, AND GAS MANAGEMENT SYSTEMS FOR RADIATION THERAPY MACHINES

(71) Applicant: Varian Medical Systems, Inc., Palo Alto, CA (US)

(72) Inventors: Ogy Sabev, San Jose, CA (US); Flavio Poehlmann-Martins, Fremont, CA (US); Reza Alibazi Behbahani, North Brunswick, NJ (US)

(73) Assignee: Varian Medical Systems, Inc., Palo Alto, CA (US)

( * ) Notice: Subject to any disclaimer, the term of this patent is extended or adjusted under 35 U.S.C. 154(b) by 571 days.

(21) Appl. No.: 18/193,709

(22) Filed: Mar. 31, 2023

(65) Prior Publication Data

US 2024/0325992 A1 Oct. 3, 2024

(51) Int. Cl.

| | |
|---|---|
| ***B01F 23/10*** | (2022.01) |
| ***A61N 5/02*** | (2006.01) |
| ***B01F 35/21*** | (2022.01) |
| ***B01F 35/221*** | (2022.01) |
| ***B01F 35/71*** | (2022.01) |
| ***B01F 35/90*** | (2022.01) |
| ***B01F 35/92*** | (2022.01) |
| ***G05D 22/02*** | (2006.01) |
| ***H01P 3/12*** | (2006.01) |
| ***H05H 9/00*** | (2006.01) |

(52) U.S. Cl.

CPC .............. *B01F 23/191* (2022.01); *A61N 5/02* (2013.01); *B01F 35/21111* (2022.01); *B01F 35/2113* (2022.01); *B01F 35/2117* (2022.01); *B01F 35/2211* (2022.01); *B01F 35/71805* (2022.01); *B01F 35/92* (2022.01); *G05D 22/02* (2013.01); *H01P 3/122* (2013.01); *B01F 2035/99* (2022.01); *H05H 9/00* (2013.01); *H05H 2277/11* (2013.01)

(58) Field of Classification Search

CPC .............. B01F 23/191; B01F 35/21111; B01F 35/2117; B01F 35/2113; B01F 35/2211; B01F 35/92; B01F 35/71805; B01F 2035/99; A61N 5/02; G05D 22/02; H01P 3/122; H05H 9/00; H05H 9/005; H05H 2277/11; H05H 2277/10

USPC .......................................................... 607/101

See application file for complete search history.

(56) References Cited

U.S. PATENT DOCUMENTS

2007/0248214 A1* 10/2007 Smith ................. A61N 5/1048 378/109

FOREIGN PATENT DOCUMENTS

WO WO-9414304 A1 * 6/1994 ........... H05H 1/0006
WO WO-2007002288 A2 * 1/2007 ................ F17C 5/06
WO WO-2022009237 A1 * 1/2022 ............... A61N 5/02

OTHER PUBLICATIONS

Technical Data; 3MTM NovecTM 5110 Insulating Gas (Year: 2021).*

* cited by examiner

*Primary Examiner* — Beverly M Flanagan

(74) *Attorney, Agent, or Firm* — Harness, Dickey & Pierce, P.L.C.

(57) ABSTRACT

A microwave network for a radiation therapy machine having a microwave source and a linear accelerator, includes a waveguide configured to connect between the microwave source and the linear accelerator. The waveguide contains at least one of a first gas or a second gas, the first gas being
(Continued)

2,3,3,3-tetrafluoro-2-(trifluoromethyl) propanenitrile and the second gas being 1,1,1,3,4,4,4-heptafluoro-3-(trifluoromethyl)-2-butanone.

18 Claims, 30 Drawing Sheets

MICROWAVE NETWORKS, WAVEGUIDES, MIXING CARTS, METHODS OF SUPPLYING GAS, AND GAS MANAGEMENT SYSTEMS FOR RADIATION THERAPY MACHINES

BACKGROUND

Field

Various example embodiments relate, in general, to radiation therapy machines, microwave networks, waveguides within the microwave networks, mixing carts and methods of supplying gases, and gas management systems for use in radiation therapy machines.

Description of Related Art

High power microwaves may be used to power linear accelerators (LINACs) that generate x-ray radiation. The microwaves may be generated using radiofrequency (RF) sources such as magnetrons and/or klystrons, and then may propagate inside hollow waveguides and directed to the LINACs.

SUMMARY

Accelerated electrons from linear accelerators (LINACs) may subsequently be used to generate the x-rays of a specific energy, for example for treatment of a patient. The LINACs may be a type of Vacuum Electron Device (VED), which uses relatively high power microwave signals to operate. These microwave signals are produced by a relatively high power microwave source, such as a klystron and/or a magnetron.

The microwave/RF power may be conducted from a source to the LINAC via a network of waveguides. While the VEDs are under ultra-high vacuum, the waveguides may be pressurized with a dielectric gas.

Electric fields inside the hollow waveguides such as those mentioned above may be relatively high. The dielectric gas may be used to reduce and/or prevent the likelihood of and/or impact from electrical breakdown in the waveguides. While traveling from the microwave source to a LINAC, these high-power microwaves may pass through various components, such as circulators, flexible waveguides, rotary joints, couplers, water loaders, phase wands, radiofrequency (RF) windows, etc. These components may generally be more vulnerable to electrical breakdown than straight waveguide sections. A dielectric gas that reduces electrical breakdown may enable the operation of microwave networks at the powers that are needed/used for radiation therapy.

Historically only sulfur hexafluoride (SF6) has been used as a dielectric gas. However, sulfur hexafluoride gas is a potent greenhouse gas and is undesirable, having a global warming harm up to 23,000 times higher than that of carbon dioxide.

At least one example embodiment provides mechanisms for utilizing gases, such as 2,3,3,3-tetrafluoro-2-(trifluoromethyl) propanenitrile (referred to as NOVEC™ 4710 or gas 4710) and/or 1,1,1,3,4,4,4-heptafluoro-3-(trifluoromethyl)-2-butanone (referred to as NOVEC™ 5110 or gas 5110) (e.g., as a dielectric gas) in radiation therapy machines (e.g., in lieu of $SF_6$).

A chemical formula for NOVEC™ 4710 may be as in Chemical Formula 1:

[Chemical Formula 1]

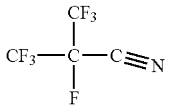

A chemical formula for NOVEC™ 5110 may be as in Chemical Formula 2:

[Chemical Formula 2]

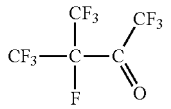

Such gases may have a reduced environmental harm as a greenhouse gas, as compared to $SF_6$.

Alternatively, or additionally, use of such gases may enable portions of waveguides within a radiation therapy system to operate at relatively high pressures.

Alternatively, or additionally, a total molar percentage of such gases may be relatively low.

Alternatively, or additionally, introduction of gases into portions of waveguides may be performed such that the total pressure of the portions of the waveguides is relatively high.

Alternatively, or additionally, different portions of a waveguide including the dielectric gases may have different total pressures.

Alternatively, or additionally, a lifetime of dielectric gases such as NOVEC™ 4710 may be enhanced using filtration and/or desiccation.

Alternatively, or additionally, a lifetime of dielectric gases such as NOVEC™ 5110 may be enhanced by reducing reflection within portions of the waveguide.

According to at least some example embodiments, a microwave network for a radiation therapy machine having a microwave source and a linear accelerator includes a waveguide configured to connect between the microwave source and the linear accelerator. The waveguide contains at least one of a first gas or a second gas, the first gas being 2,3,3,3-tetrafluoro-2-(trifluoromethyl) propanenitrile and the second gas being 1,1,1,3,4,4,4-heptafluoro-3-(trifluoromethyl)-2-butanone.

In some example embodiments, the waveguide includes the first gas and a carrier gas, and a molar percentage of the carrier gas in at least a portion of the waveguide is between about 60% and about 90%.

In some example embodiments, the carrier gas is carbon dioxide, a molar percentage of the first gas within the portion of the waveguide is between about 13.5% and about 16.5%, and a total pressure in the portion of the waveguide is between about 27.5 pound force per square inch gauge (psig) and about 32.5 psig.

In some example embodiments, a total pressure of at least a portion of the waveguide containing at least one of the first gas or the second gas is less than about 90 psig.

In some example embodiments, at least a portion of the waveguide includes an ultraviolet mitigation component.

In some example embodiments, the ultraviolet mitigation component includes a coating on an inner wall of the portion, the coating being antireflective with respect to ultraviolet radiation.

In some example embodiments, the coating is a dielectric.

Alternatively, or additionally, according to at least some example embodiments, a waveguide for use in a radiation therapy machine includes a first portion configured to be under vacuum during operation of the radiation therapy machine, a second portion in series with the first portion, the second portion configured to be at a first pressure, a first radiofrequency (RF) window between the first portion and the second portion, a third portion in series with the second portion, the third portion configured to be at a second pressure, the second pressure greater than the first pressure, and a second RF window between the second portion and the third portion.

In some example embodiments, the first pressure is between about 27.5 psig and about 32.5 psig.

In some example embodiments, the second pressure is between about 57.5 psig and about 62.5 psig.

In some example embodiments, the waveguide may include a fourth portion in series with the third portion, the fourth portion configured to be at the first pressure, and a third RF window between the third portion and the fourth portion.

In some example embodiments, the waveguide may include a fifth portion in series with the fourth portion, the fifth portion configured to be under vacuum during operation of the radiation therapy machine, and a fourth RF window between the fourth portion and the fifth portion.

In some example embodiments, the first portion is configured to receive microwave radiation from a microwave source, and the fifth portion is configured to output the microwave radiation to a linear accelerator.

Alternatively, or additionally, according to at least some example embodiments, a microwave network for a radiation therapy machine includes a flex guide including a corrugated thin wall and an exoskeletal flexible structure surrounding the corrugated thin wall.

In some example embodiments, the exoskeletal flexible structure is configured to reduce a bulge of the flex guide when a pressure of a portion surrounded by the corrugated thin wall is greater than atmospheric pressure.

Alternatively, or additionally, according to at least some example embodiments, a mass-flow mixing cart to supply gases to a waveguide for a radiation therapy system includes a vacuum pump. a first valve connected to the vacuum pump, the first valve configured to control a vacuum pressure of at least a portion of the waveguide, a second valve configured to control introduction of a first gas into the portion of the waveguide, the first gas being one of 2,3,3,3-tetrafluoro-2-(trifluoromethyl) propanenitrile or 1,1,1,3,4,4,4-heptafluoro-3-(trifluoromethyl)-2-butanone, and a third valve configured to control an introduction of a second gas into the portion of the waveguide, the second gas being a carrier gas.

In some example embodiments, the mixing cart may include a first mass flow meter connected to the first valve, the first mass flow meter configured to measure a flowrate of the first gas, and a second mass flow meter connected to the second valve, the second mass flow meter configured to measure a flowrate of the second gas.

In some example embodiments, the mixing cart may include a first gauge configured to measure a pressure of the portion of the waveguide.

In some example embodiments, the mixing cart may include a reservoir connected to the first valve and to the second valve, the reservoir configured to store a mixture of the first gas and the second gas.

In some example embodiments, the mixing cart may include a reservoir heater at least partially surrounding the reservoir, and configured to heat the reservoir.

In some example embodiments, the mixing cart may include a refrigerant scale configured to hold the reservoir.

Alternatively, or additionally, according to at least some example embodiments, a method of supplying a gas to a portion of a waveguide for a radiation therapy machine includes supplying a first gas to a piping that is in fluid communication with the portion of the waveguide, the first gas being one of 2,3,3,3-tetrafluoro-2-(trifluoromethyl) propanenitrile or 1,1,1,3,4,4,4-heptafluoro-3-(trifluoromethyl)-2-butanone, and supplying a carrier gas to the piping.

According to some example embodiments, the method may include supplying the first gas into a reservoir, supplying the carrier gas into the reservoir until at least one of a total weight of the reservoir reaches a threshold weight or a total pressure of the reservoir reaches a threshold pressure, and supplying a mixture of the first gas and the carrier gas from the reservoir into the portion of the waveguide.

In some example embodiments, the method may include heating a bottle with water from the radiation therapy machine, and introducing the first gas from the bottle to the piping.

Alternatively, or additionally, according to at least some example embodiments, a gas management system for a microwave network including a waveguide includes a gas management device configured to adjust a characteristic of a gas in the waveguide, and a first radiofrequency (RF)-blocking interface in fluid communication with the waveguide and with the gas management device, the first RF-blocking interface defining a plurality of vents, the plurality of vents configured to suppress radiofrequency wave from flowing into the gas management device and configured to allow the gas to enter the gas management device.

Although example embodiments are described with reference to dielectric gases such as NOVEC™ 4710 and/or NOVEC™ 5110, example embodiments are not limited to the above. For example, any suitable gas, such as but not limited to octafluoropropane ($C_3F_8$) and/or another environmentally friendly gas such as an environmentally friendly fluorocarbon, may be used as a dielectric gas within a waveguide for a radiation therapy machine, in lieu of sulfur hexafluoride ($SF_6$), with the same or similar mixing process and/or the same overall handling within a radiation therapy machine as those described with reference to gases NOVEC™ 4710 and/or NOVEC™ 5110.

For example, other gases may be used as a dielectric gas in various example embodiments, such as gases comprising large, dense molecules having a short mean-free path of stray electrons. The shorter mean-free path may help stop or reduce electron flow, which may help reduce the likelihood of arcing. For example, dielectric gases having halogens such as fluorine, chlorine, bromine, or iodine may be used, as the halogens are highly electro-negative and may help capture stray electrons and reduce the propensity for arcing within the radiation therapy machine.

BRIEF DESCRIPTION OF DRAWINGS

Example embodiments will be more clearly understood from the following detailed description taken in conjunction with the accompanying drawings, which represent non-limiting example embodiments as described herein, wherein.

DETAILED DESCRIPTION

Figure 1:
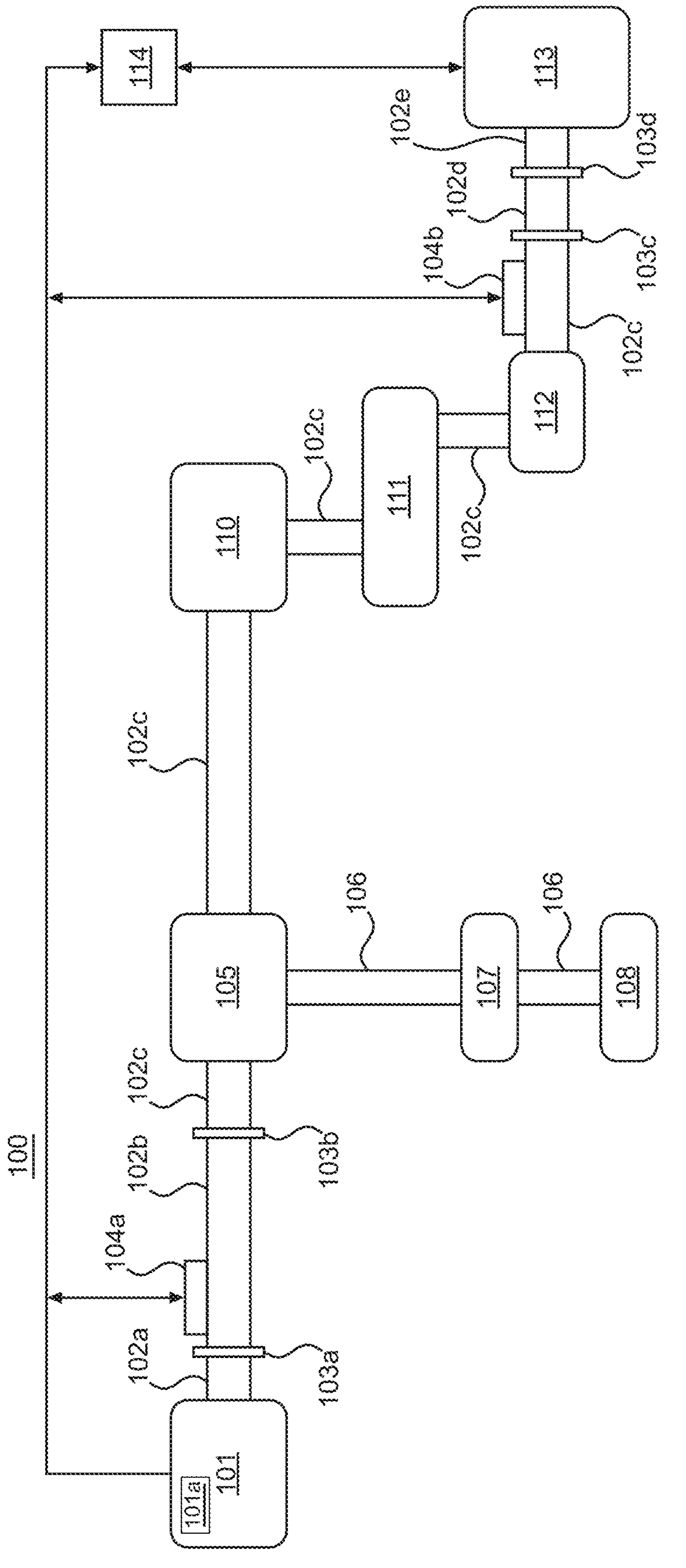
FIGS. 1 and 2 illustrate a portion of radiation therapy machine, according to various example embodiments.

Various example embodiments will now be described more fully with reference to the accompanying drawings in which some example embodiments are illustrated.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Independent of the grammatical term usage, individuals with male, female or other gender identities are included within the term.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing elements or control nodes. Such existing hardware may include one or more Central Processing Units (CPUs), system on chips (SoCs), digital signal processors (DSPs), application-specific-integrated-circuits, field programmable gate arrays (FPGAs) computers or the like.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of example embodiments are typically encoded on some form of tangible, recording, or non-transitory storage medium. The storage medium may be read only, random access memory, system memory, cache memory, magnetic (e.g., a floppy disk, a hard drive, MRAM), optical media, flash memory, buffer, combinations thereof, or other devices for storing data or video information magnetic (e.g., a floppy disk or a hard drive) or optical (e.g., a compact disk read only memory, or "CD ROM"). Example embodiments are not limited by these aspects of any given implementation.

FIG. 1 illustrates a portion of a radiation therapy machine according to various example embodiments.

Referring to FIG. 1, a radiation therapy machine 100 may include a radiofrequency (RF) source 101, a plurality of waveguide portions 102*a*-102*e*, a plurality of RF windows 103*a*-103*d*, a circulator 105, a reflected power waveguide branch 106, a phase wand 107, a water load 108, an electric or magnetic (E or H) waveguide bend 110, a rotary joint 111, a flex guide 112 and a LINAC 113. The radiation therapy machine 100 may further include a plurality of directional couplers 104*a* and 104*b*. There may be a controller 114 such as a processor or other processing circuitry in communication with the RF source 101, the LINAC 113, and the directional couplers 104*a* and 104*b*. The controller 114 may control operation of the radiation therapy machine 100.

In some example embodiments, the directional couplers 104*a* and 104*b* may be used to detect microwave power flow and/or to distinguish between power flowing forward from reflected power flowing the other way at the same time within the waveguide. This may be done via sampling a relatively small amount of the power and discriminating forward versus backward direction. The detected power may be used for controlling the system, such as reducing and/or minimizing the reflection by tuning the RF source frequency to more closely match the accelerator resonance frequency.

The waveguide portions 102*a*-102*e* may include a first waveguide portion 102*a*, a second waveguide portion 102*b*, a third waveguide portion 102*c*, a fourth waveguide portion 102*d*, and a fifth waveguide portion 102*e*. Example embodiments are not limited thereto, however, and there may be more or less waveguide portions than illustrated.

Adjacent ones of the waveguide portions 102*a*-102*e* may be arranged in a serial manner. For example, the first waveguide portion 102*a* may be arranged in series with the second waveguide portion 102*b*, the second waveguide portion 102*b* may be arranged in series with the third waveguide portion 102*c*, the third waveguide portion 102*c* may be arranged in series with the fourth waveguide portion 102*d*, and the fourth waveguide portion 102*d* may be arranged in series with the fifth waveguide portion 102*e*.

The plurality of RF windows 103*a*-103*d* may include a first RF window 103*a*, a second RF window 103*b*, a third RF window 103*c* and a fourth RF window 103*d*.

The RF source 101 may be or may include a source of RF energy, such as electromagnetic energy in the radio wave and/or microwave spectrum. For example, the RF source 101 may be or may include at least one of a magnetron or a klystron. The RF source 101 may generate electromagnetic radiation, and the electromagnetic radiation may propagate through the radiation therapy machine 100 to the LINAC 113 via the plurality of waveguide portions 102*a*-102*e*. The RF source 101 may include a water supply 101*a*, such as a cooling water supply 101*a* that includes water at a temperature of about 40° C. The water supply 101*a* will be discussed later.

In more detail with regard to the example embodiment shown in FIG. 1, the first waveguide portion 102*a* may be coupled or directly coupled to the RF source 101 and the second waveguide portion 102*b*. The first waveguide portion 102*a* may be configured to propagate microwave and/or other electromagnetic radiation output from the RF source 101 to the second waveguide portion 102*b*. The first RF window 103*a* may be arranged between the first waveguide portion 102*a* and the second waveguide portion 102*b*.

The second waveguide portion 102*b* may be coupled to or directly coupled to the first waveguide portion 102*a* and the third waveguide portion 102*c*. The second waveguide portion 102*b* may be configured to propagate the microwave and/or other electromagnetic radiation from the first waveguide portion 102*a* to the third waveguide portion 102*c*.

The second RF window 103*b* may be arranged between the second waveguide portion 102*b* and the third waveguide portion 102*c*.

The third waveguide portion 102*c* may be coupled to or directly coupled to the second waveguide portion 102*b* and the fourth waveguide portion 102*d*. The third waveguide portion 102*c* may be configured to propagate the microwave and/or other electromagnetic radiation from the second waveguide portion 102*b* to the fourth waveguide portion 102*d*.

The third RF window 103*c* may be arranged between the third waveguide portion 102*c* and the fourth waveguide portion 102*d*. Additionally, the circulator 105, the electric or magnetic (E or H) waveguide bend 110, the rotary joint 111, and the flex guide 112 may be arranged at various locations along the third waveguide portion 102*c*.

The fourth waveguide portion 102*d* may be coupled to or directly coupled to the third waveguide portion 102*c* and the fifth waveguide portion 102*e*. The fourth waveguide portion 102*d* may be configured to propagate the microwave and/or other electromagnetic radiation from the third waveguide portion 102*c* to the fifth waveguide portion 102*e*. The fourth RF window 103*d* may be arranged between the fourth waveguide portion 102*d* and the fifth waveguide portion 102*e*.

The fifth waveguide portion 102*e* may be coupled to or directly coupled to the fourth waveguide portion 102*d* and the LINAC 113. The fifth waveguide portion 102*e* may be configured to propagate the microwave and/or other electromagnetic radiation from the fourth waveguide portion 102*d* to the LINAC 113.

The reflected power waveguide branch 106 may extend between the circulator 105 and the water load 108. The phase wand 107 may be arranged along the reflected power waveguide branch 106 between the circulator 105 and the water load 108.

In at least some example embodiments, second waveguide portion 102*b* and fourth waveguide portion 102*d* may be connected or in fluid communication with each other, for example with a hose (not illustrated). In at least some example embodiments, second waveguide portion 102*b* and fourth waveguide portion 102*d* may be connected so that a pressure in the second waveguide portion is equal to or substantially equal to a pressure in the fourth waveguide 102*d*; however, example embodiments are not limited thereto.

A length of each of the waveguide portions 102*a*-102*e* may be the same or substantially the same. Alternatively, a length of at least one of the waveguide portions 102*a*-102*e* may be different than one or more others of the waveguide portions 102*a*-102*e*. Alternatively, or additionally, a cross-sectional diameter or cross-sectional area of each of the plurality of waveguide portions 102*a*-102*e* may be the same, or substantially the same, or alternatively a cross-sectional diameter or cross-sectional area of at least one of the waveguide portions 102*a*-102*e* may be different than one or more others of the waveguide portions 102*a*-102*e*. In at least some example embodiments, a length of a waveguide portion 102*a*-102*e* may be a multiple of a half-wavelength of microwave radiation generated by the RF source 101. Each of, or at least one of, the waveguide portions 102*a*-102*e* may be about ⅓ of a meter to about one meter. According to at least some example embodiments, RF components such as waveguides may be configured as multiples of ¼ or ½ of the wavelength of the RF signal propagated inside the waveguide. Doing so may, for example, match power flow through discontinuities such as RF windows or changes in waveguide cross-sectional area.

Each of, or at least one of, the RF windows 103*a*-103*d* may be composed of a material that enables transmission of electromagnetic radiation generated by the RF source 101. For example, each of, or at least one of, the RF windows 103*a*-103*d* may be composed of a ceramic; however, example embodiments are not limited thereto. A thickness and/or a material of each of the RF windows 103*a*-103*d* may be the same, or substantially the same. Alternatively, a thickness and/or a material of at least one of the RF windows 103*a*-103*d* may be different than a respective thickness and/or material of one or more others of the RF windows 103*a*-103*d*. Each of, or at least one of, the RF windows 103*a*-103*d* may be a relatively thin disk pillbox window. In some example embodiments, sides of the RF windows 103*a*-103*d* may have a section of circular waveguide forming a resonator cavity. The ceramic may be relatively thin to not interfere with the RF energy, or to marginally interfere with the RF. The ceramic may be thick enough to withstand or at least partially withstand stresses involved. For example, the RF windows 103*a*-103*d* may be on the order of about 0.3175 cm (⅛ inch) thick, but example embodiments are not limited thereto.

Each of, or at least one of, the RF windows 103*a*-103*d* may enable separate waveguide portions 102*a*-102*e* to be at different pressures and/or temperatures. For example, waveguide portion 102*b* may be sealed by first RF window 103*a* and second RF window 103*b* such that waveguide portion 102*b* may be at a different total pressure than that of waveguide portion 102*a* and/or waveguide portion 102*c*.

In at least some example embodiments, during operation of the radiation therapy machine 100, first waveguide portion 102*a* and fifth waveguide portion 102*e* may be maintained at a vacuum pressure.

In at least some example embodiments, during operation of the radiation therapy machine 100 and/or in standby of the radiation therapy machine 100, the second waveguide portion 102*b* and the fourth waveguide portion 102*d* may be filled (or at least partially filled) with a gas such as NOVEC™ 4710 and/or NOVEC™ 5110.

In at least some example embodiments, during operation of the radiation therapy machine 100 and/or in standby of the radiation therapy machine 100, a total pressure of the second waveguide portion 102*b* and/or a total pressure of the fourth waveguide portion 102*d* may be less than about 90 psig (e.g., may be between about 27.5 pounds per square inch gauge (psig) and about 32.5 psig). For example, a total pressure of the second waveguide portion 102*b* may be about 30 psig. As used below, one psig is equal to or substantially equal to 6.897 kilopascals.

In at least some example embodiments, a total pressure of the fourth waveguide portion 102*d* may be the same or substantially the same as a total pressure of the second waveguide portion 102*b* (e.g., when the radiation therapy machine 100 is in operation or in standby).

In at least some example embodiments, a total pressure of the third waveguide portion 102*c* may be between about 55 psig and about 65 psig (e.g., may be about 60 psig), for example, when the radiation therapy machine 100 is in operation or in standby.

The power holdoff capability of gases such as NOVEC™ 4710 and/or NOVEC™ 5110 increase with pressure. Accordingly, higher pressures (e.g., about 60 psig) in waveguide portions most subject to arcing (e.g., waveguide portions 102*c*, 106, etc.) may be desirable to reduce and/or minimize holdoff breakdown. However, a RF window between a waveguide portion at vacuum pressure and a waveguide portion at the above-mentioned higher pressure may break when subjected to this relatively high pressure differential. Moreover, waveguide portions may deform under relatively high internal pressures. To address these issues, one or more example embodiments may utilize relatively high pressure gas mixtures at waveguide portions more subject to arcing (e.g., waveguide portions 102*c*, 106, etc.), and utilize a step-wise increase in pressures from the vacuum pressure (e.g., in first waveguide portion 102*a*) to the relatively high pressure in the waveguide portions most subject to arcing (e.g., third waveguide portion 102*c*). In this regard, for example, the second waveguide portion 102*b* may have a pressure between vacuum pressure and the pressure at the third waveguide portion 102*c* such that the RF windows between adjacent waveguide portions are subject to manageable pressure differentials (e.g., about 30 psig).

Similarly, one or more example embodiments may utilize a step-wise decrease in pressures from the relatively high pressure in the waveguide portions most subject to arcing (e.g., third waveguide portion 102*c*) to the vacuum pressure (e.g., in fifth waveguide portion 102*e*). In this example, the fourth waveguide portion 102*d* may have a pressure between the pressure at the third waveguide portion 102*c* and the vacuum pressure at the fifth waveguide portion 102*e*. Additionally, or alternatively, as discussed herein, external reinforcement of waveguides (e.g., in the form of an exoskeleton) may be provided to reduce and/or minimize deformation of the waveguides.

In one example, the first waveguide portion 102*a* may be at or near vacuum pressure, the second waveguide portion 102*b* may have a total pressure of about 30 psig, and the third waveguide portion 102*c* have a total pressure of about 60 psig, such that the step-wise increase in pressures from the first waveguide portion 102*a* to the third waveguide portion 102*c* is vacuum->30 psig->60 psig.

Similarly, the third waveguide portion 102*c* have a total pressure of about 60 psig, the fourth waveguide portion 102*d* may have a total pressure of about 30 psig and the fifth waveguide portion 102*e* may be at vacuum pressure such that the step-wise decrease in pressures from the third waveguide portion 102*c* to the fifth waveguide portion 102*d* is 60 psig→30 psig→vacuum.

According to one or more example embodiments, a total pressure of any of the waveguide portions 102*a*-102*e* may be less than about 90 psig, which may be based on structural properties of the waveguide portions 102*a*-102*e* and/or of the RF windows 103*a*-103*d*.

In at least some example embodiments, at least one of the second waveguide portion 102*b*, the third waveguide portion 102*c*, or the fourth waveguide portion 102*d* may have a carrier gas such as carbon dioxide and/or nitrogen gas included therein. In at least some example embodiments, a molar percentage of gas such as NOVEC™ 4710 and/or NOVEC™ 5110 may be between about 13.5% and about 16.5% within at least one of the second waveguide portion 102*b*, the third waveguide portion 102*c*, or the fourth waveguide portion 102*d*. In some example embodiments, a molar percentage of the carrier gas may be between about 50% and about 95%, e.g. about 83.5% to 86.5%.

In some example embodiments, the molar percentage of the at least one first gas or second gas may range from about 10% to about 40%. In some example embodiments, improved or optimal performance may be obtained with a molar percentage of the at least one first gas or second gas being about 15%, for example as tested on a Varian™ radiation therapy machine.

In some example embodiments, the waveguide portions 102*b*-102*d* may include an active gas such as NOVEC™ 4710 and a carrier gas such as $CO_2$. In some example embodiments, there may not be another gas other than the active gas and the carrier gas that is included in the waveguide portions 102*b*-102*d*, and the sum of the molar percentages of the active gas and the carrier gas may be 100%. The total mass of the active gas and carrier gas that is included in the respective waveguide portions 102*b*-102*d* may be based on the respective molecular masses of the active gas and the carrier gas and on the respective molar percentages of the active gas and the carrier gas. If different carrier gases and/or different active gases are used, the total mass ratio may change while the respective molar percentages of the active and carrier gases in the mixture are maintained. Thus, the composition of the components of the mixture may be defined as molar percentages.

In at least some example embodiments, one or more of the RF windows 103*a*-103*d* separating individual waveguide portions 102*a*-102*e* may be omitted. Adjacent waveguide portions 102*a*-102*e* may also be permanently sealed and prefilled. According to some example embodiments, the waveguide portions 102*b* and 102*d* may be integrated to allow microwaves to travel through the intermediate section in modes that are less likely to produce breakdown (e.g. in a circular mode (a TE11 mode)).

In at least some example embodiments, at least one of the circulator 105, the phase wand 107, the water load 108, the E or H waveguide bend 110, the rotary joint 111, or the flex guide 112 may be included or in communication with the third waveguide portion 102*c*; however, example embodiments are not limited thereto.

Figure 2:
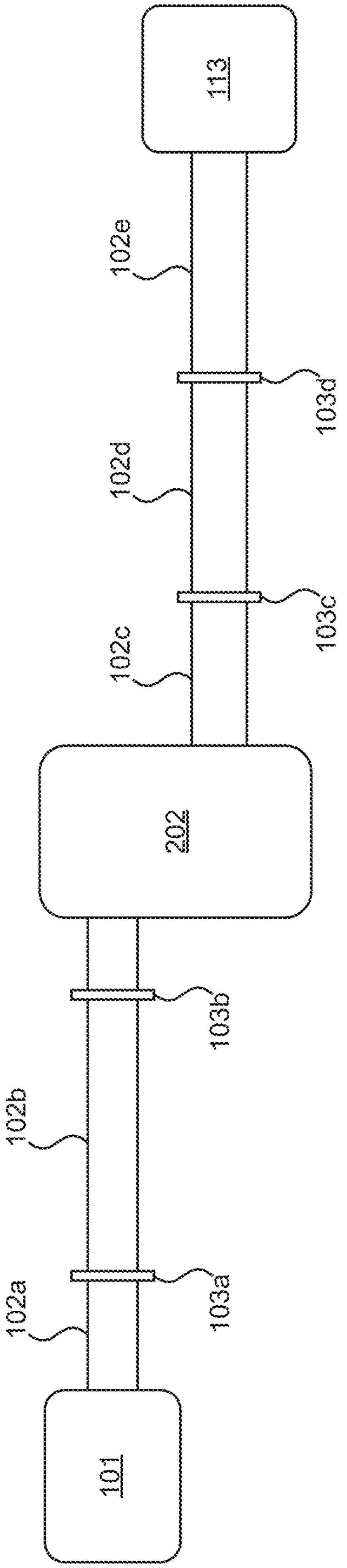

FIG. 2 is a simplified illustration of the portion radiation therapy machine shown in FIG. 1.

In FIG. 2, for simplicity, the circulator 105, the phase wand 107, the water load 108, the E or H waveguide bend 110, the rotary joint 111, and the flex guide 112 described with reference to FIG. 1 are illustrated as network components 202. More generally, in at least some example embodiments, network components 202 may include components that may be susceptible to electrical breakdown (e.g., may be more susceptible to electrical breakdown than other components in the radiation therapy machine 100 such as components that may be included in straight waveguide portions such as the second waveguide portion 102*b* and/or the fourth waveguide portion 102*d*).

In at least some example embodiments, dielectric gases such as NOVEC™ 4710 and/or NOVEC™ 5110 may be included in the third waveguide portion 102*c* to help prevent and/or reduce the likelihood of, and/or impact from, electrical breakdown of components such as the network components 202.

Figure 3:
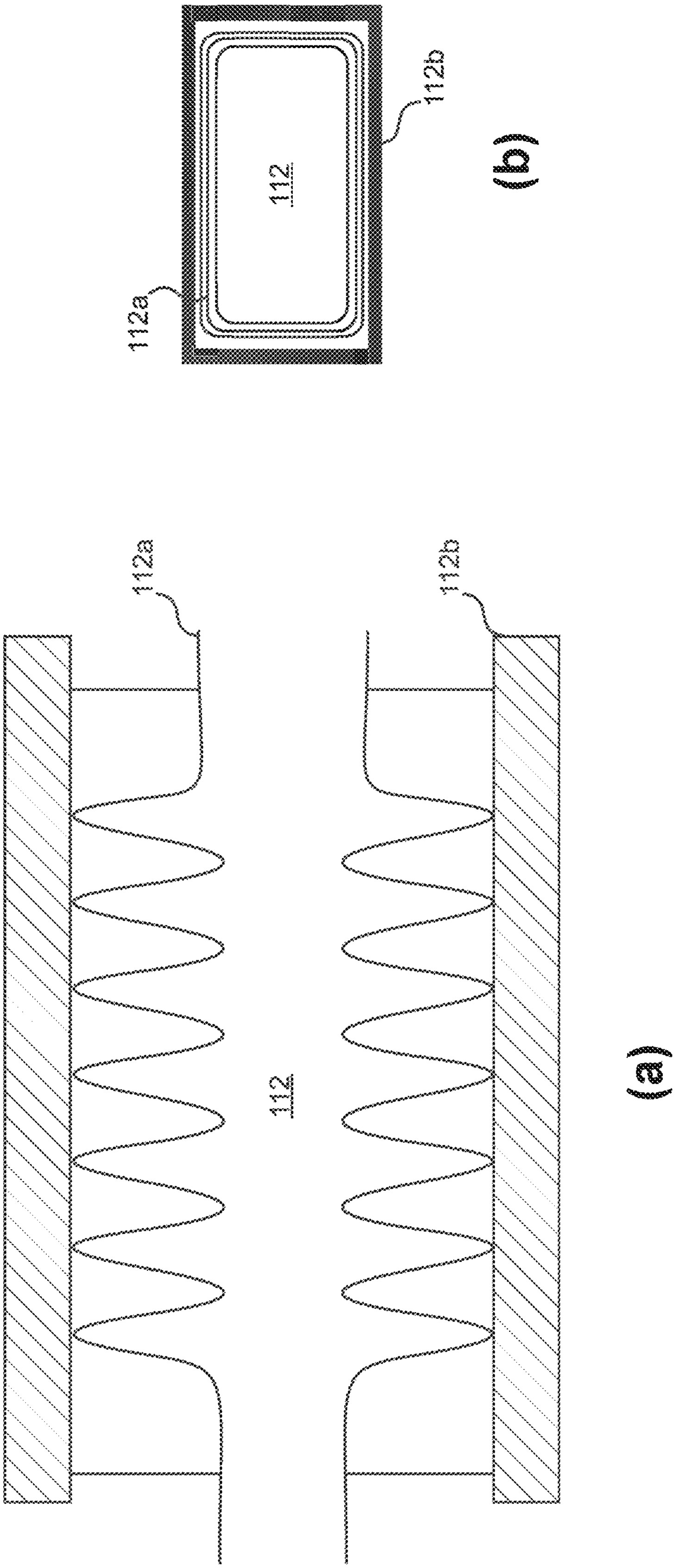
FIG. 3 illustrates a flex guide for use in a radiation therapy machine, according to various example embodiments.

FIG. 3 illustrates a side view and a cross-sectional view of the flex guide 112 according to some example embodiments.

Referring to FIG. 3, the flex guide 112 used in the radiation therapy machine may be semi-rigid. In at least some example embodiments, the flex guide 112 may include a corrugated thin wall 112*a* as in the side-view (a) and the cross-sectional view (b). In at least some example embodiments, the flex guide 112 may further include an exoskeletal brace structure 112*b*.

The corrugated thin wall 112*a* may be an inner wall of the flex guide 112. The corrugated thin wall 112*a* may have an accordion shape, and may be at least partly flexible.

In some example embodiments, the corrugated thin wall 112*a* may be made of a thin sheet metal. The corrugation may allow for some structural rigidity in addition to flexibility. In some example embodiments, components of the corrugated thin wall 112*a* may be soldered and/or welded together.

The exoskeletal brace structure 112*b* may be articulated with the flex guide 112. The exoskeletal brace structure 112*b* may be rigid and may not allow, or may reduce the allowance of, the flex guide 112 from bulging at the middle under higher pressures, for example under the third higher pressures of the waveguide portion 102*c* (in FIG. 1).

In one example, the exoskeletal brace structure 112*b* may be a drag chain and/or cable carrier that at least partially constrains an accordion shape of the walls of the flex guide 112 on the top and bottom.

FIGS. 4A-6H illustrate mixing carts and methods of introducing gases to a portion of a waveguide, according to various example embodiments.

For convenience of description, example embodiments are illustrated such that a mixing cart is connected to, or in fluid communication with, the third waveguide portion 102*c*; however, in at least some example embodiments, the mixing cart may be connected to or in fluid communication with other waveguide portions (e.g., waveguide portions 102*b*, 102*d*). The mixing cart may be connected to waveguide portions, such as the third waveguide portion 102*c*, through an aperture 415 in the waveguide portion 102*c*. There may be a hose and/or a piping, such as piping 440, connected to the waveguide portion 102*c* through the aperture 415.

Also, for convenience, FIGS. 4A-6H describe methods of introducing gases to a portion of a waveguide that may be or may already have been evacuated; however, example embodiments are not limited thereto.

Referring to FIGS. 4A-4H, a mixing cart 499 may include a first bottle 401, a bottle heater 421, a second bottle 402, a vacuum pump or vacuum 403, a first valve 404, a second valve 405, a third valve 406, a fourth valve 407, first and second gauges 411 and 412, a first mass flow meter (MFM) 413, second MFM 414, a first pressure regulator 418, and a second pressure regulator 419. In some example embodiments, the second pressure regulator 419 may be a heated pressure regulator.

There may be one or more methods or approaches to introducing and maintaining gases such as NOVEC™ 4710 or NOVEC™ 5110 along with carrier gases into waveguide portions such as waveguide portion 102*c*. In at least some example embodiments, a controller 450, which may be or include a programmable logic controller (PLC), laptop, other computer device, may control and/or communicate with any or all of the various components of the mixing cart 499 such as various valves and/or meters. The controller 450 may be in communication, e.g. in electrical communication and/or mechanical communication, with regulators and/or valves and/or gauges and/or MFM's and/or vacuums, such as at least one of the vacuum 403, the first through fourth valve 404-407, the first and second gauges 411 and 412, the first and second MFM's 4113 and 1414, and the first and second pressure regulators 418 and 419. In one example, the controller 450 may be used in conjunction with one or more solenoid actuators to control the components of the mixing cart 499. The communication of the controller 450 may be wired and/or wireless. The controller 450 may send and/or receive commands and/or data from any or all of the components of the mixing cart 499. In at least some example embodiments, the controller 450 may execute a set of computer-readable instructions to control introduction and maintenance of gases such as NOVEC™ 4710 and/or NOVEC™ 5110 into a waveguide portion such as waveguide portion 102*c*. In at least some example embodiments, a user, such as an operator and/or a technician such as a field service technician, may perform or at least partially perform one or more of the functions described below.

In at least some example embodiments, the first bottle 401 may include either NOVEC™ 4710 or NOVEC™ 5110, and may or may not contain other components. Either or both of NOVEC™ 4710 and NOVEC™ 5110 may be stored as a liquid and/or a gas.

In at least some example embodiments, the first bottle 401 may be surrounded by bottle heater 421. In some example embodiments, the bottle heater 421 may be or may include a heated blanket.

In at least some example embodiments, the bottle heater 421 may be composed of cooling lines and/or a bladder. In this example, water may be supplied through a connection 460, which may be used as to heat the first bottle 401. The water, which may be at a temperature of about 40° C., may be the cooling water from, or directly from, the water supply 101*a*, which may be made to flow around the first bottle 401 with the cooling lines and/or the bladder as part of the system flow loop. The cooling water from the connection 460 may provide a source of regulated heat to the first bottle 401.

In at least some example embodiments, the second bottle 402 may store a carrier, such as a carrier gas. The carrier gas may include a gas such as carbon dioxide and/or nitrogen.

In at least some example embodiments, the first and second pressure regulators 418 and 419 may be included to regulate pressures from the first gas bottle 401 and the second gas bottle 402. In at least some example embodiments, the second pressure regulator 419 include an electrical resistive heater (not shown) which may allow expanding gases to be heated as they expand, which may counteract cooling effects of an expanding, heated gas. In at least some example embodiments, either or both of the first and second pressure regulators 418 and 419 may be upstream from, or downstream from, respective second and third valves 405 and 406.

Figure 4A:
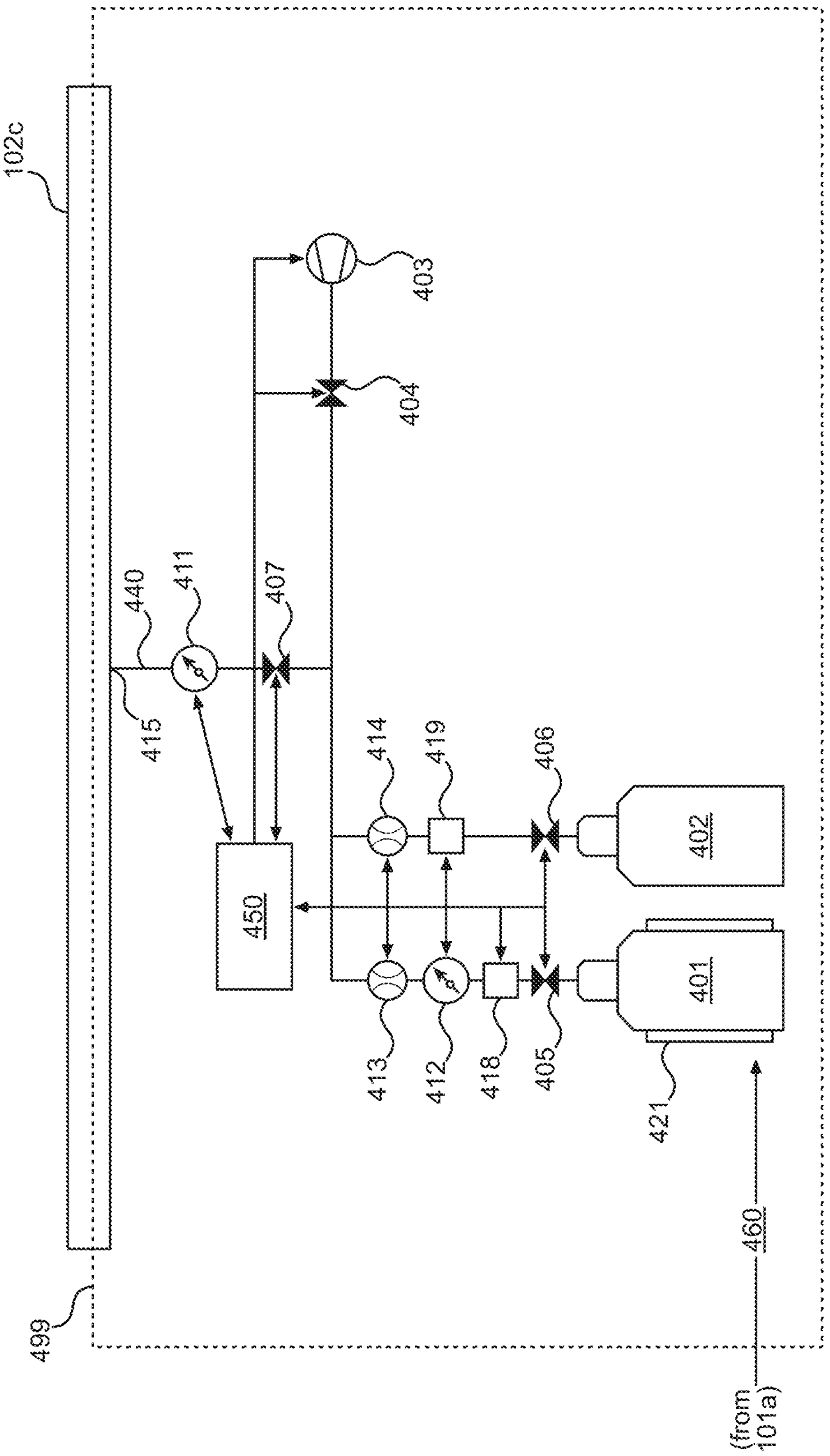
FIGS. 4A-4H illustrate a mixing cart and a method of introducing gases to a portion of a waveguide, according to various example embodiments.

Referring to FIG. 4A, initially each of valves 404, 405, and 406 may be switched off, and the waveguide portion 102*c* may not be in fluid communication with the first and second bottles 401 and 402. The waveguide portion 102*c* may be at an initial pressure.

Figure 4B:
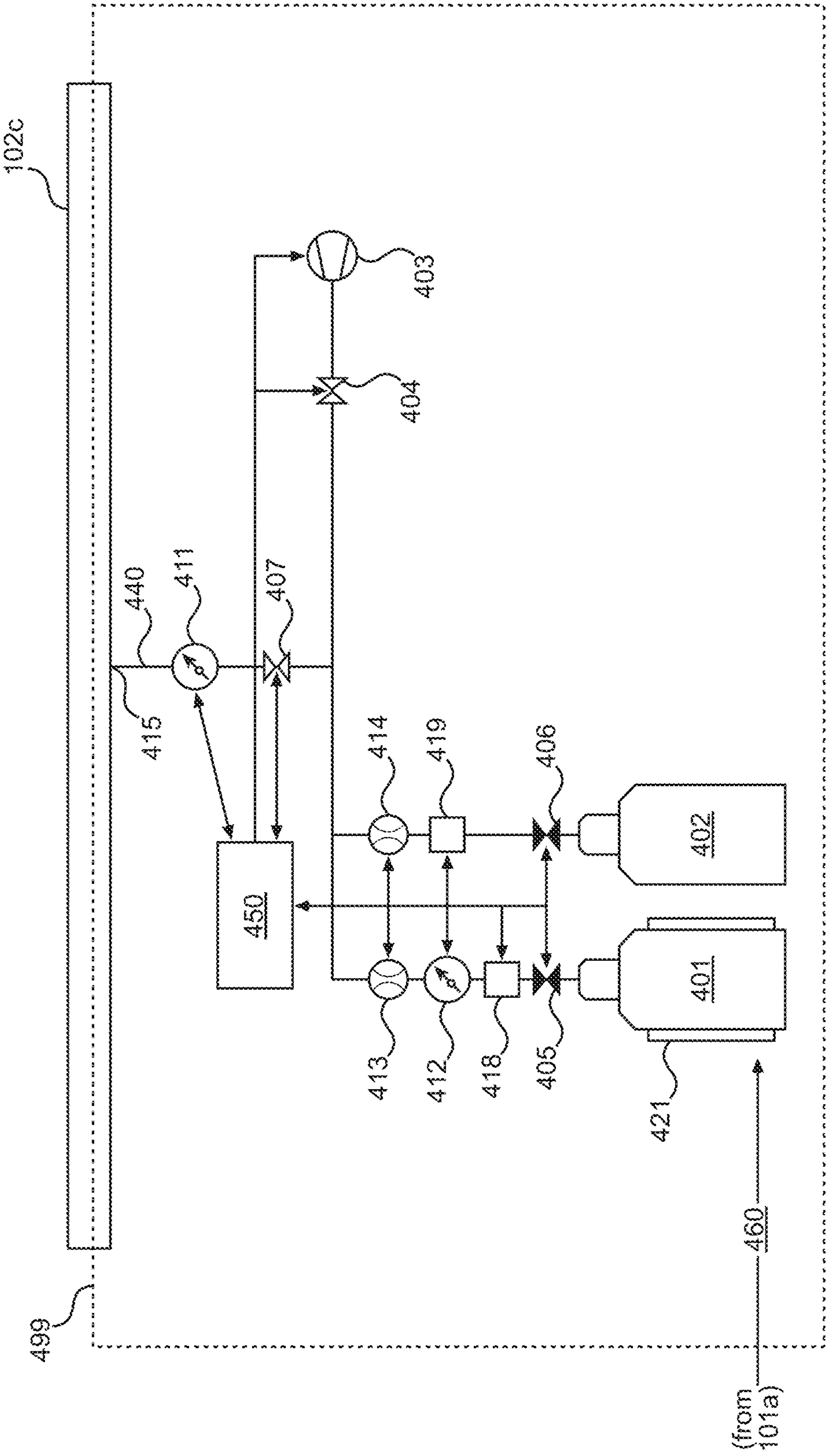

Referring to FIG. 4B, the first valve 404 and the fourth valve 407 may be opened, and the vacuum 403 may be activated. The first valve 404 may be opened before or after the fourth valve 407. The vacuum 403 may be activated after both the first valve 404 and the fourth valve 407 are opened, and may reduce pressure in the waveguide portion 102*c*, for example to a vacuum pressure. The pressure may be determined according to the first gauge 411.

Figure 4C:
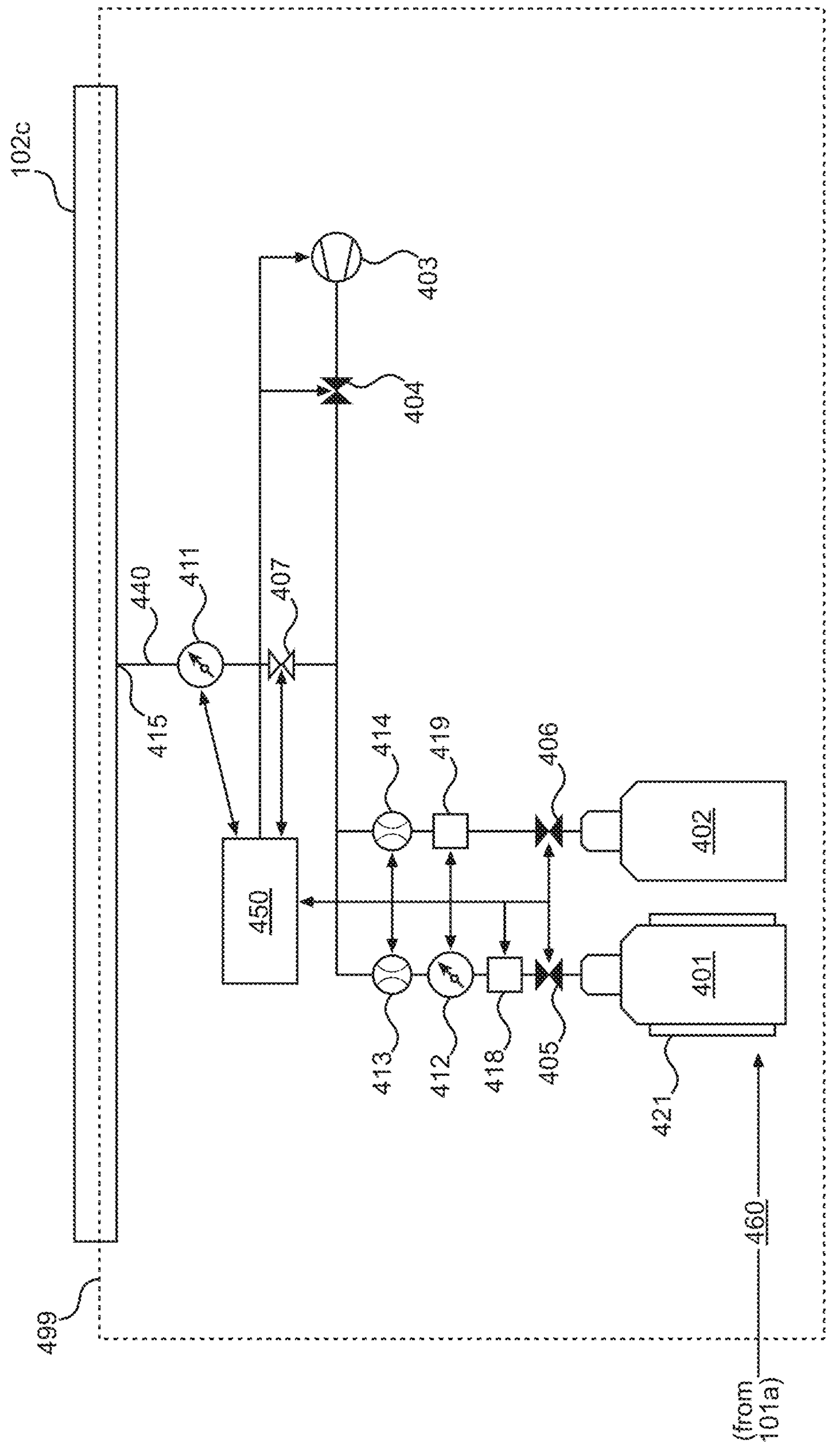

Referring to FIG. 4C, the first valve 404 may be closed or switched off, for example, when the first gauge 411 indicates that the waveguide portion 102*c* is at a desired pressure. The desired pressure may correspond to a vacuum or desired vacuum in the waveguide portion 102*c*; however, example embodiments are not limited thereto. In another example, the first valve 404 may be programmed to switch off after expiration of a time interval required to reach desired vacuum levels, which may be determined through empirical experimentation.

Figure 4D:
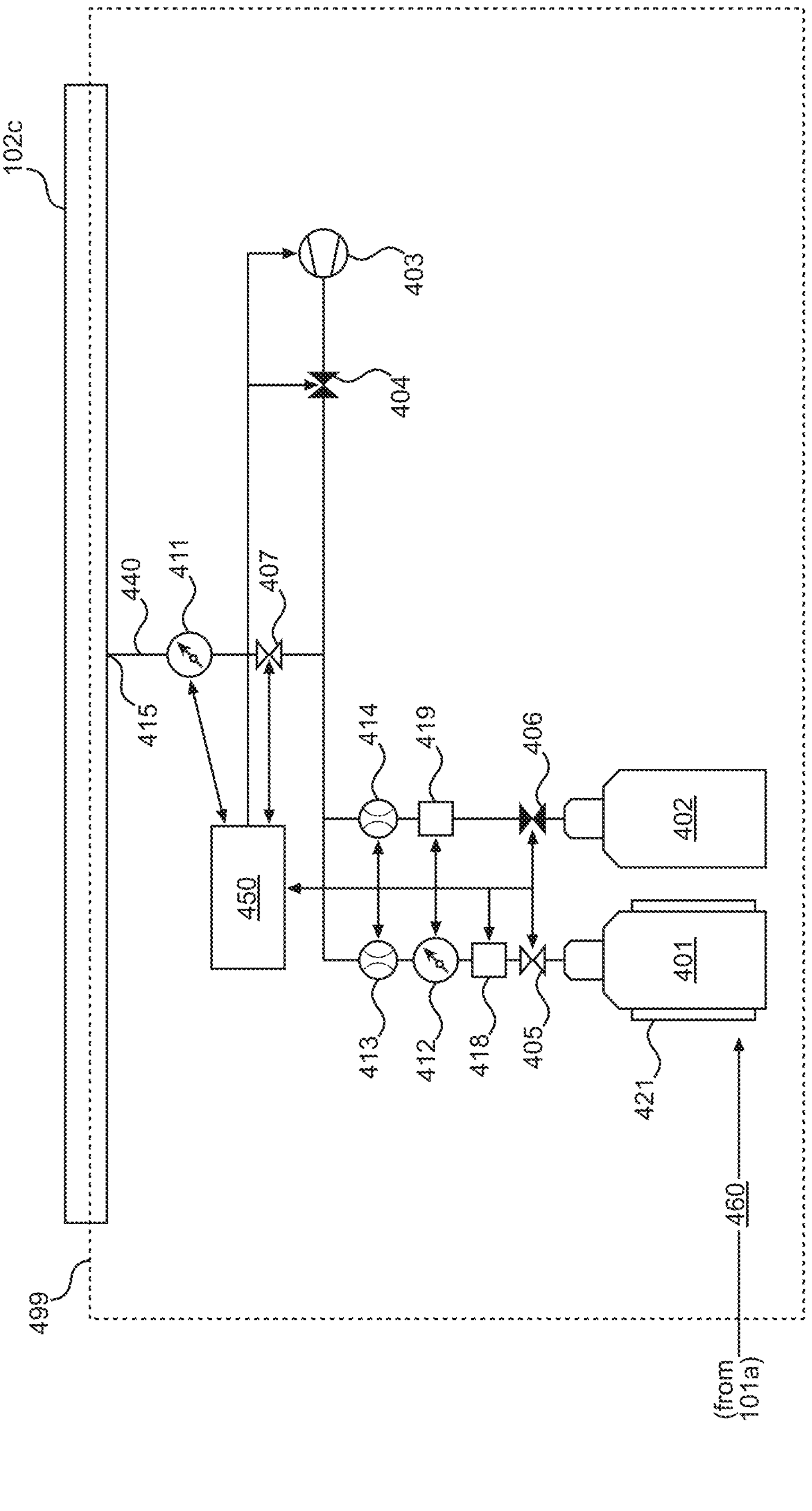

Referring to FIG. 4D, the second valve 405 may be opened or switched on. In at least some example embodiments, the second valve 405 may be opened when or after the bottle 401 has reached a particular temperature. The particular temperature may be greater than and/or may be determined based on the boiling point of either or both of NOVEC™ 4710 or NOVEC™ 5110. A gas, such as a gas of either or both of NOVEC™ 4710 or NOVEC™ 5110 from the first bottle 401, may be regulated with the first pressure regulator 418; however, example embodiments are not limited thereto. In an example embodiment in which a heated blanket is used, a thermostat or potentiometer may be used to provide a known amount of input heat. In another example, the cooling water of the system may be used to determine the temperature of the bottle 401 (e.g., after a determined period of time, the bottle 401 is determined to have reached the particular temperature.

Figure 4E:
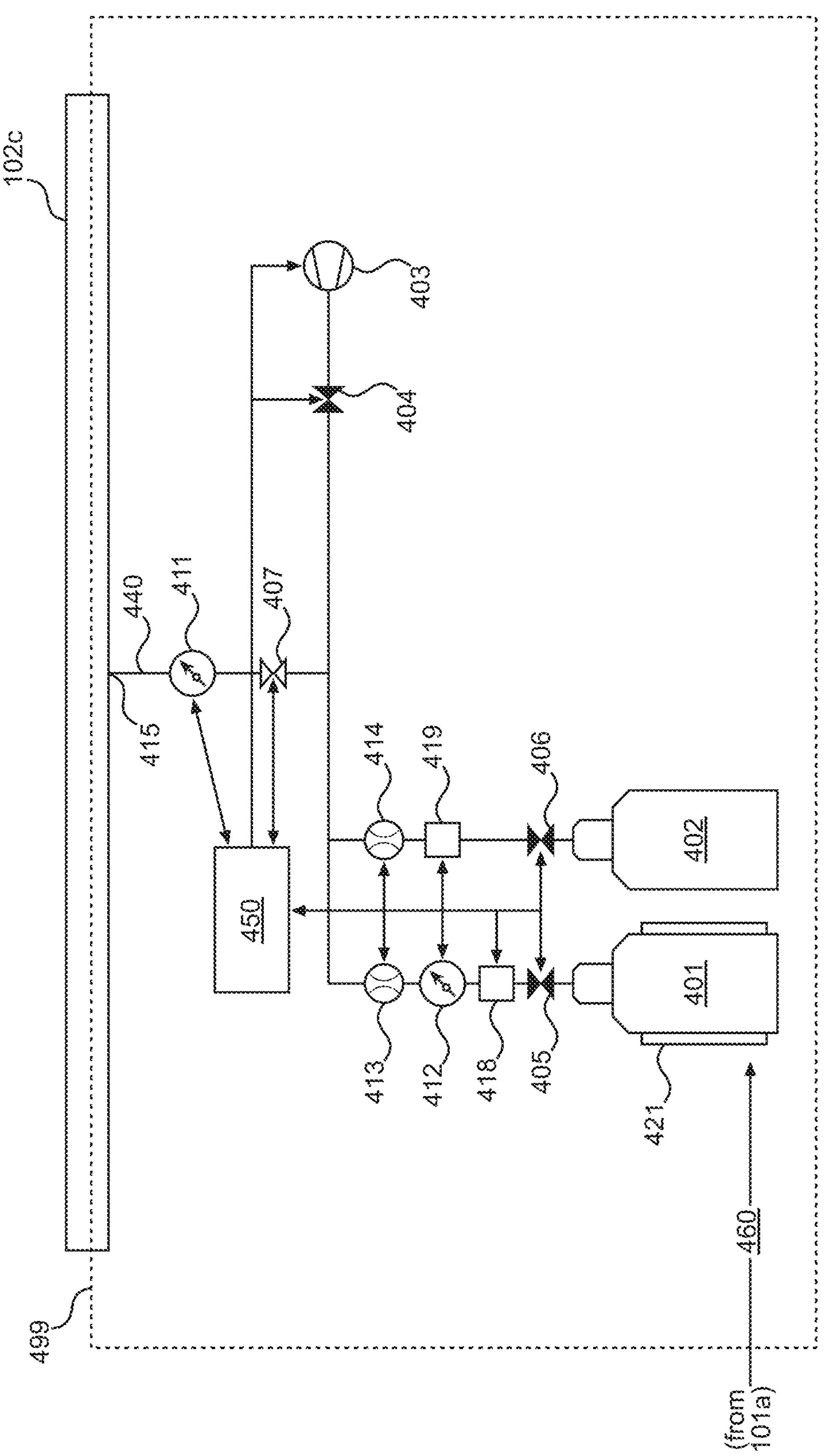

Referring to FIG. 4E, the MFM 413 may indicate a metered out amount of gaseous NOVEC™ 4710 and/or NOVEC™ 5110. The particular amount of gaseous NOVEC™ 4710 and/or NOVEC™ 5110 may be determined by a desired pressure within the waveguide portion 102*c*, which may be measured by the first gauge 411. In at least some example embodiments, once the particular amount of gaseous NOVEC™ 4710 or NOVEC™ 5110 has been metered, second valve 405 may be closed or switched off.

Figure 4F:
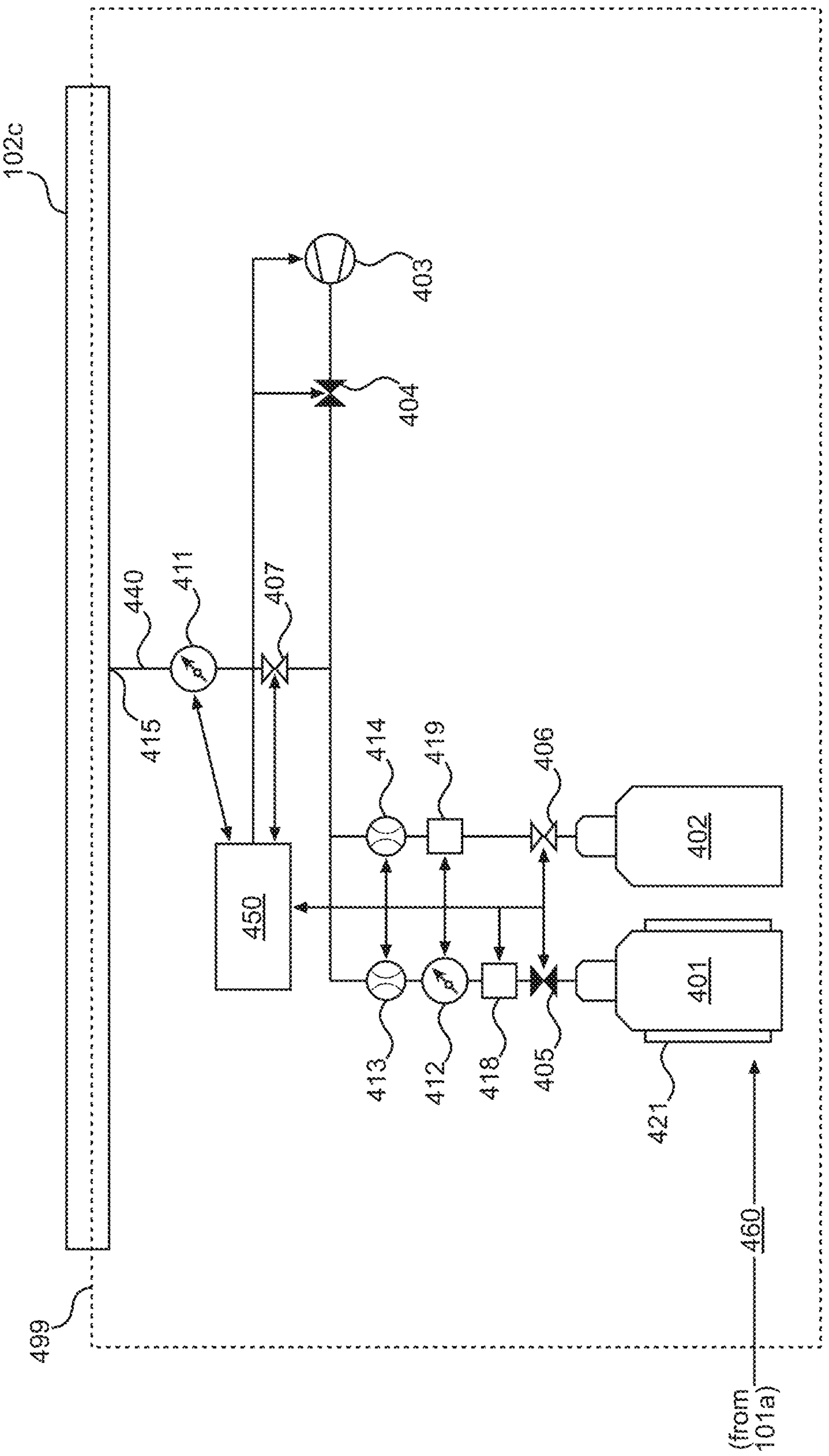

Referring to FIG. 4F, the third valve 406 may be opened, introducing an amount of carrier gas from the second bottle 402. The amount of carrier gas may be measured and metered with the second MFM 414. The amount of carrier gas may be based on a desired pressure and/or a desired concentration or desired molar percentage of gaseous NOVEC™ 4710 or NOVEC™ 5110 within the waveguide portion 102*c*. Although discussed as being introduced afterwards, in at least some example embodiments, the carrier gas from the second bottle 402 may be introduced before, and/or concurrently with and/or iteratively with, introduction of NOVEC™ 4710 or NOVEC™ 5110 into the third waveguide portion 102*c*.

Figure 4G:
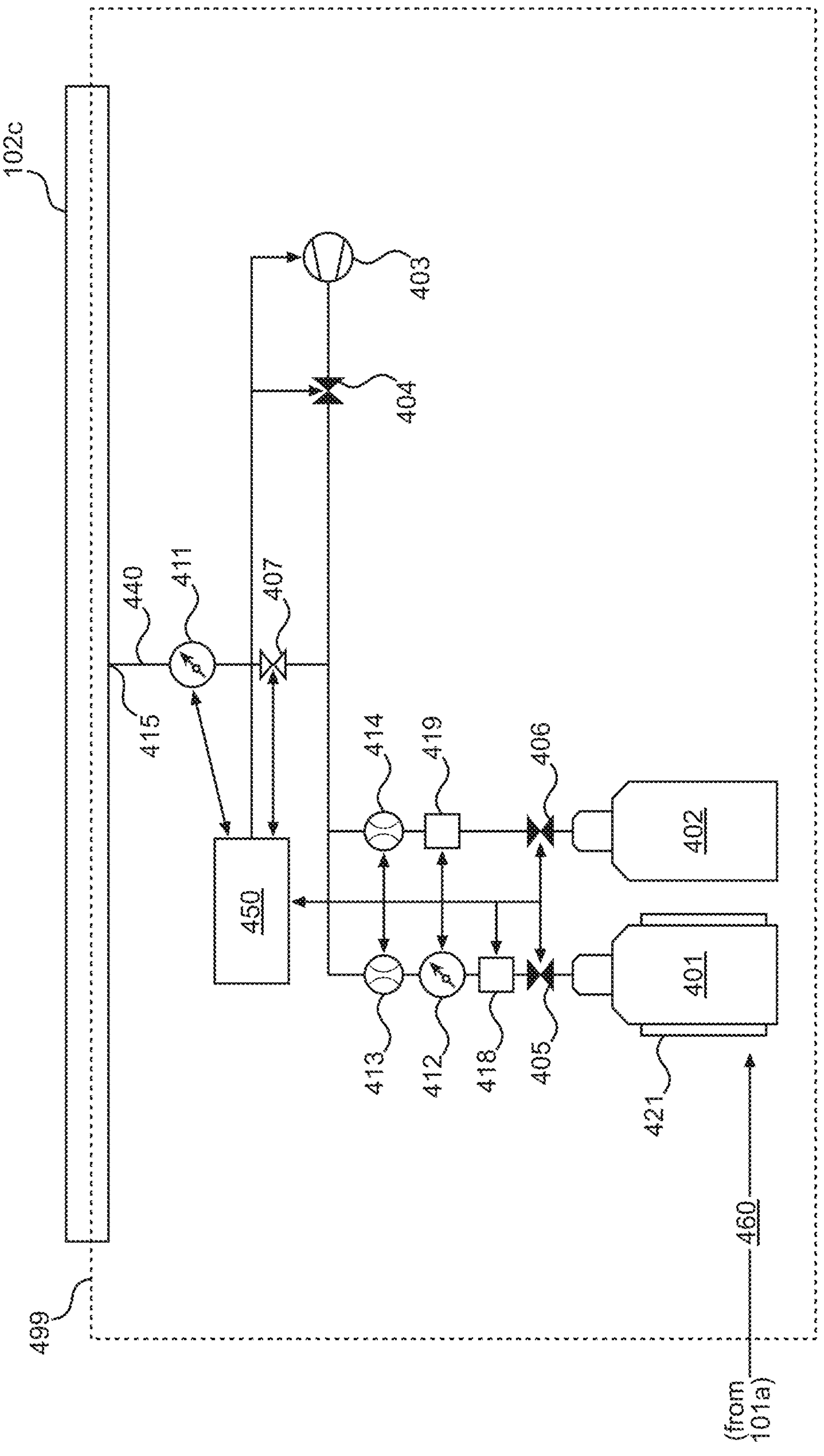

Referring to FIG. 4G, based on a reading of a pressure in the third waveguide portion 102*c* from the first gauge 411, the third valve 406 may be closed or switched off. The pressure in the waveguide portion 102*c* may indicate a pressure of the mix of gaseous NOVEC™ 4710 or NOVEC™ 5110 and the carrier gas. In at least some example embodiments, the pressure in the waveguide portion 102*c* may be about 60 psig+/−about 2.5 psig; however, example embodiments are not limited thereto.

Although FIG. 4G illustrates the mixing cart 499 connected to the waveguide portion 102*c*, example embodiments are not limited thereto. For example, in at least some example embodiments, the mixing cart 499 may be connected to either or both of waveguide portion 102*b* and 102*d*, and the pressure within the waveguide portion 102*b* and/or 102*d* may be about 30 psig+/−about 2.5 psig.

Figure 4H:
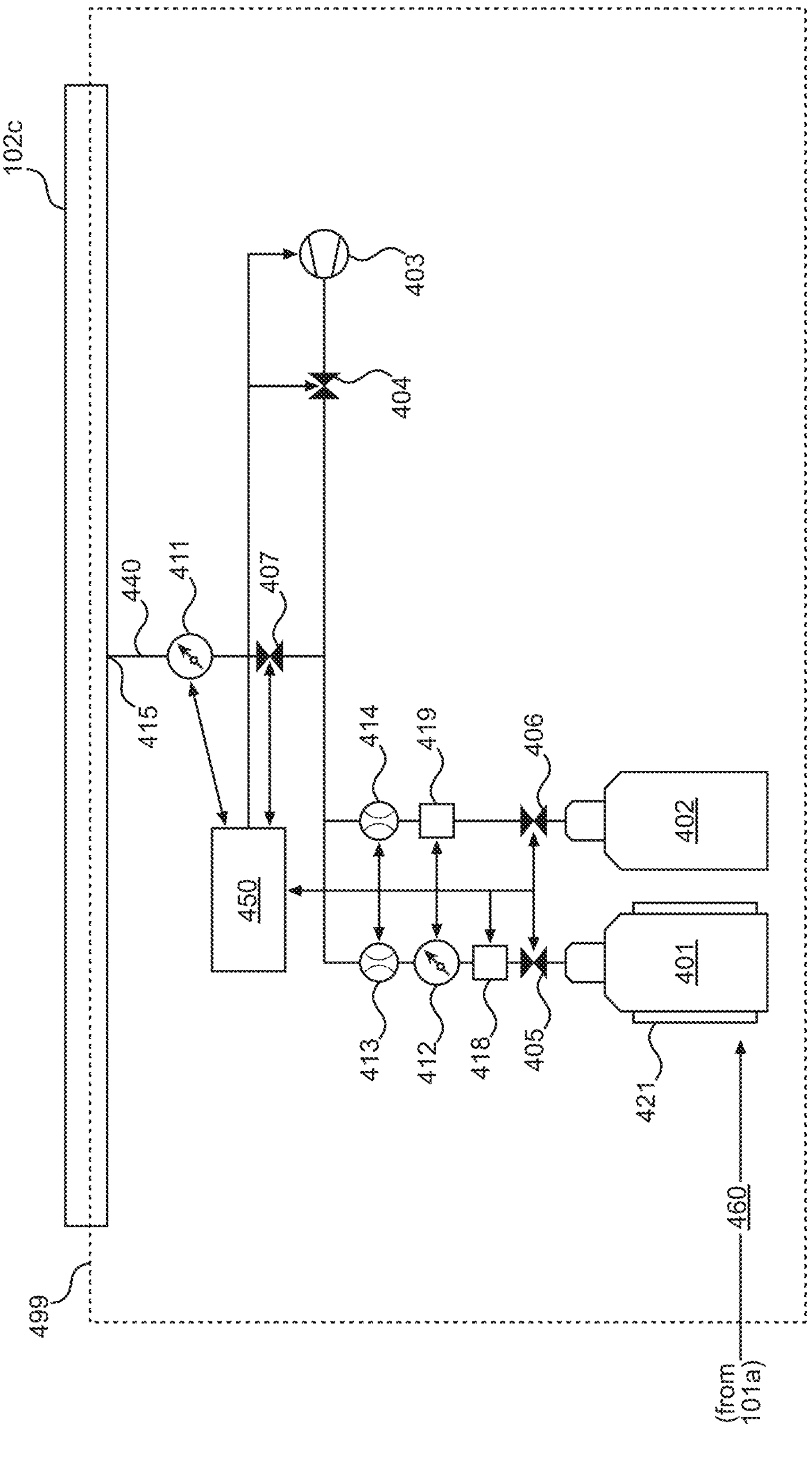

Referring to FIG. 4H, the fourth valve 407 may be switched off, based on a reading of the first gauge 411. In at least some example embodiments, the second gauge 412 may actuate and/or control the fourth valve 407; however, example embodiments are not limited thereto.

FIGS. 5A-5H illustrate the mixing cart 499 and a method of introducing gases to a portion of a waveguide, according to various example embodiments. For brevity of explanation, descriptions of like components relative to other examples are omitted. The controller 450 may control and/or communicate with any or all of the various components of the mixing cart shown in FIGS. 5A-5H in the same or substantially the same manner as discussed above with regard to FIGS. 4A-4H.

Referring to FIGS. 5A-5H, the mixing cart 599 may include a reservoir 420, along with a reservoir heater 422. Although not shown, the example embodiment shown in FIGS. 5A-5H may include flow meters such as MFM 413 and/or MFM 414 illustrated in FIGS. 4A-4H. Moreover, although not shown, lines such as line 501 connecting the first bottle 401 to the second gauge 412 may be heated.

Figure 5A:
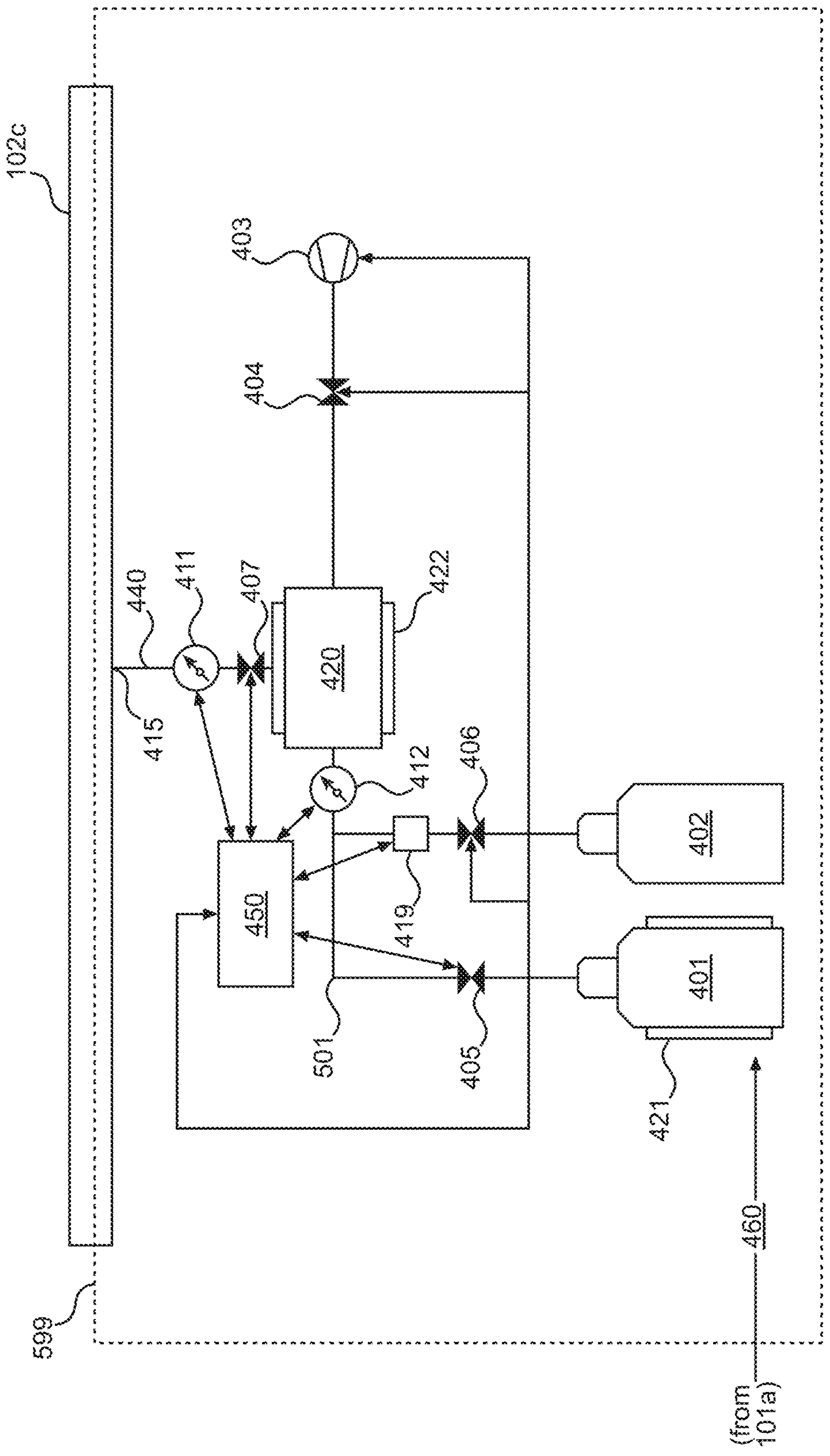
FIGS. 5A-5H illustrate a mixing cart and a method of introducing gases to a portion of an evacuated waveguide, according to various example embodiments.

Referring to FIG. 5A, initially each of the first to fourth valves 404, 405, 406, and 407 may be switched off.

Figure 5B:
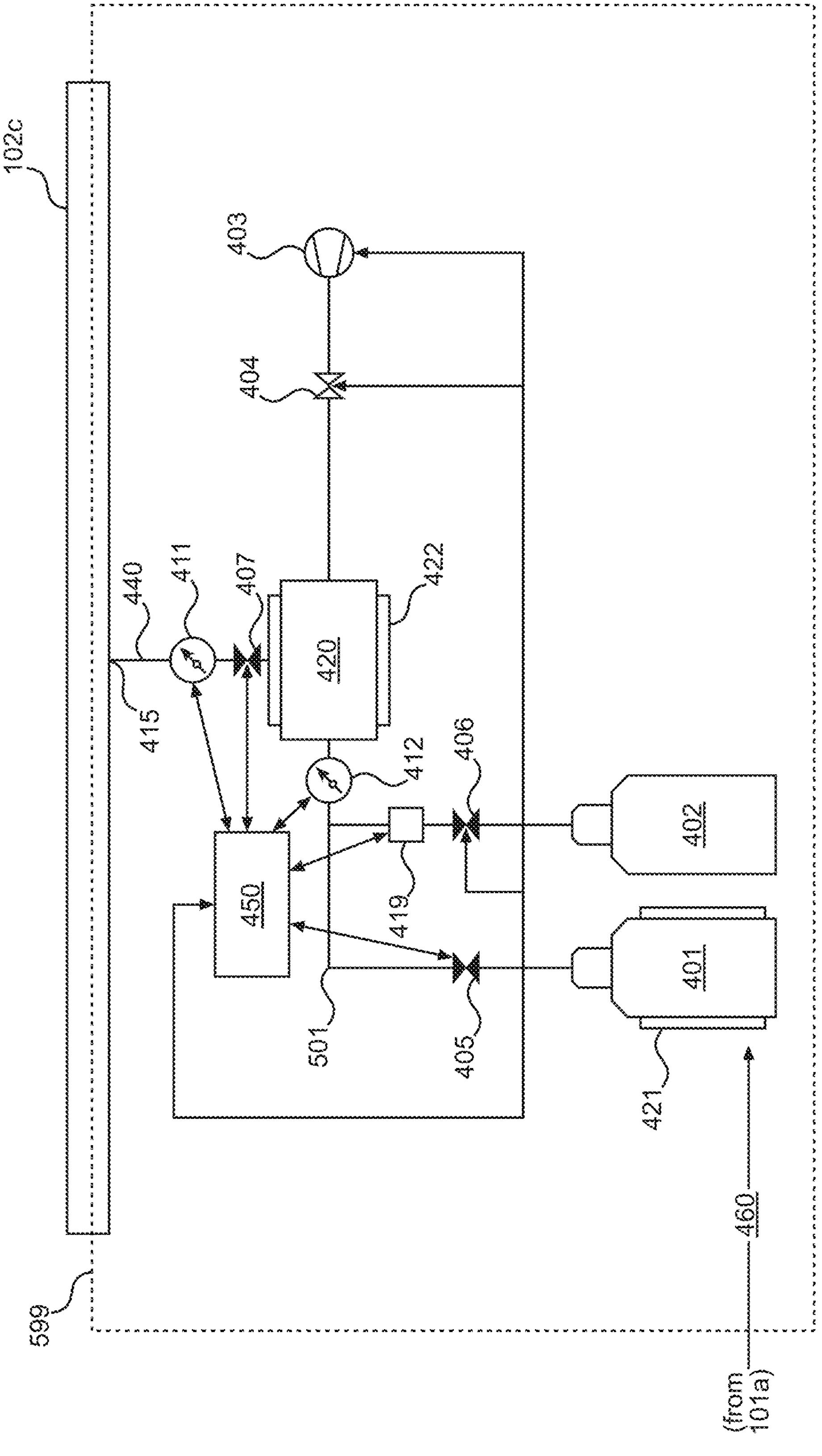

Referring to FIG. 5B, first valve 404 may be turned on, and before, after, or concurrently with the first valve being turned on, the vacuum 403 may be activated and a pressure in the reservoir 420 may be reduced. Before, after, or concurrently with the pressure in the reservoir 420 being reduced, the reservoir heater 422 may be turned or switched on.

Figure 5C:
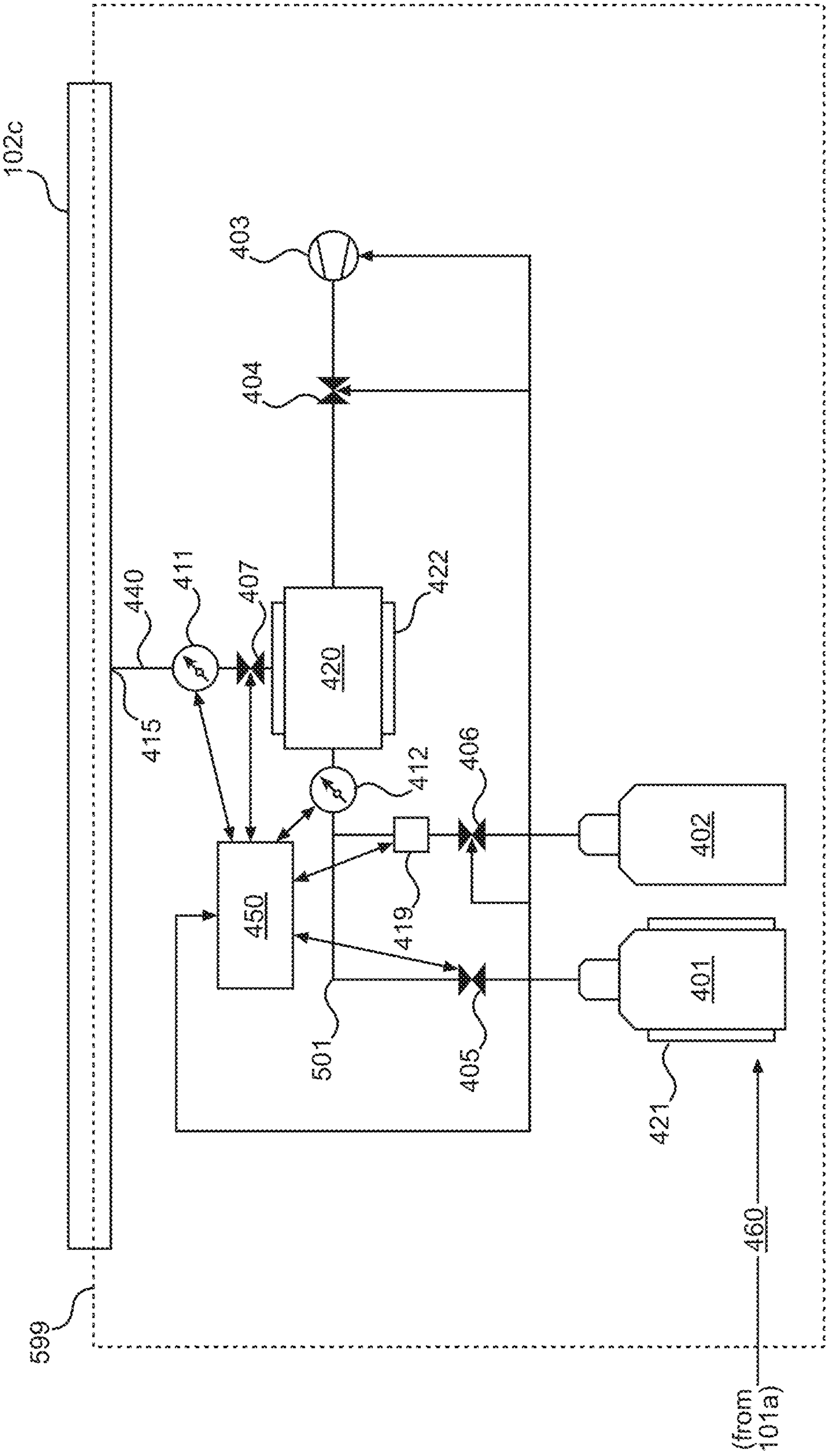

Referring to FIG. 5C, the first valve 404 may be turned or switched off when a pressure in the reservoir 420 reaches a particular pressure, e.g. a particular vacuum pressure. During this phase, the gauge 412 reflects the pressure in the reservoir 420. Later, the gauge 412 depicts the partial pressure of the cylinder as each gas is added in. In some example embodiments, the vacuum 403 may be deactivated before, after, or concurrently with the switching off of the first valve 404.

Figure 5D:
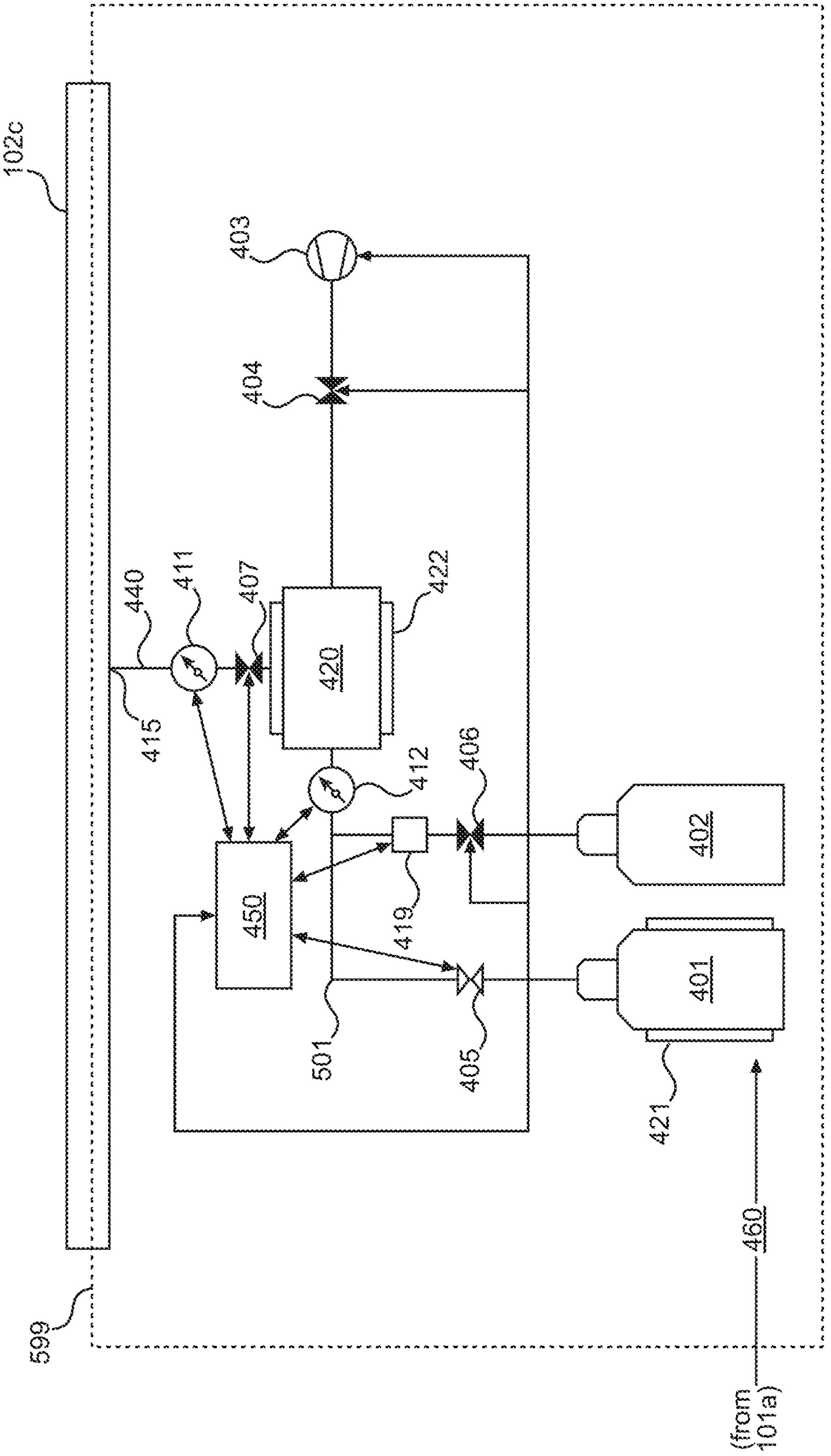

Referring to FIG. 5D, the second valve 405 may be opened to supply either or both of gaseous NOVEC™ 4710 or NOVEC™ 5110 to the reservoir 420.

Figure 5E:
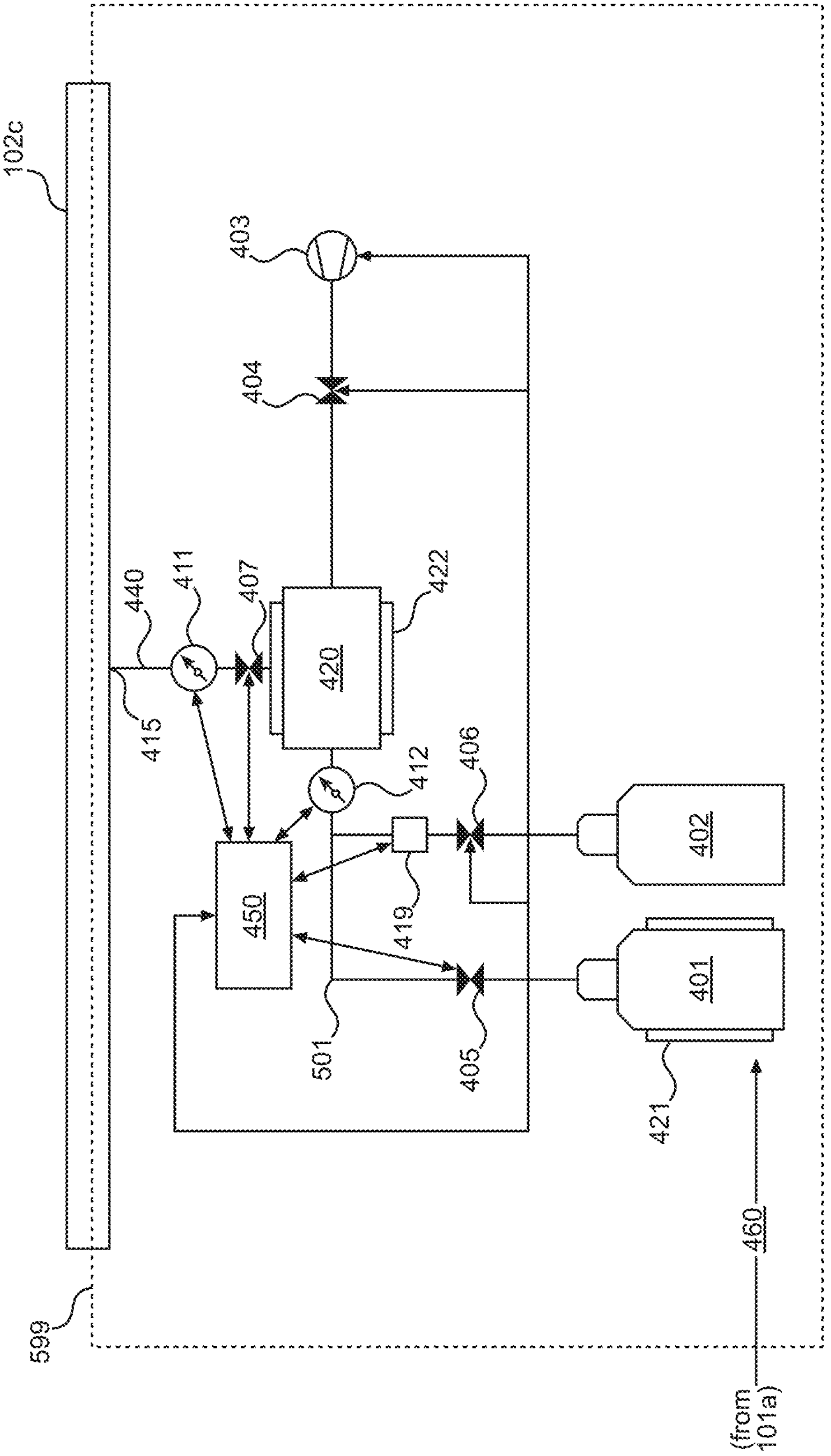

Referring to FIG. 5E, the first valve 405 may be turned or switched off. In at least some example embodiments, the first valve 405 may be turned off when a pressure within the reservoir 420 reaches a particular pressure. The particular pressure may be measured by the second gauge 412; however, example embodiments are not limited thereto. In some example embodiments, the particular pressure may be based on a volume and/or a temperature of the reservoir 420; however, example embodiments are not limited thereto.

Figure 5F:
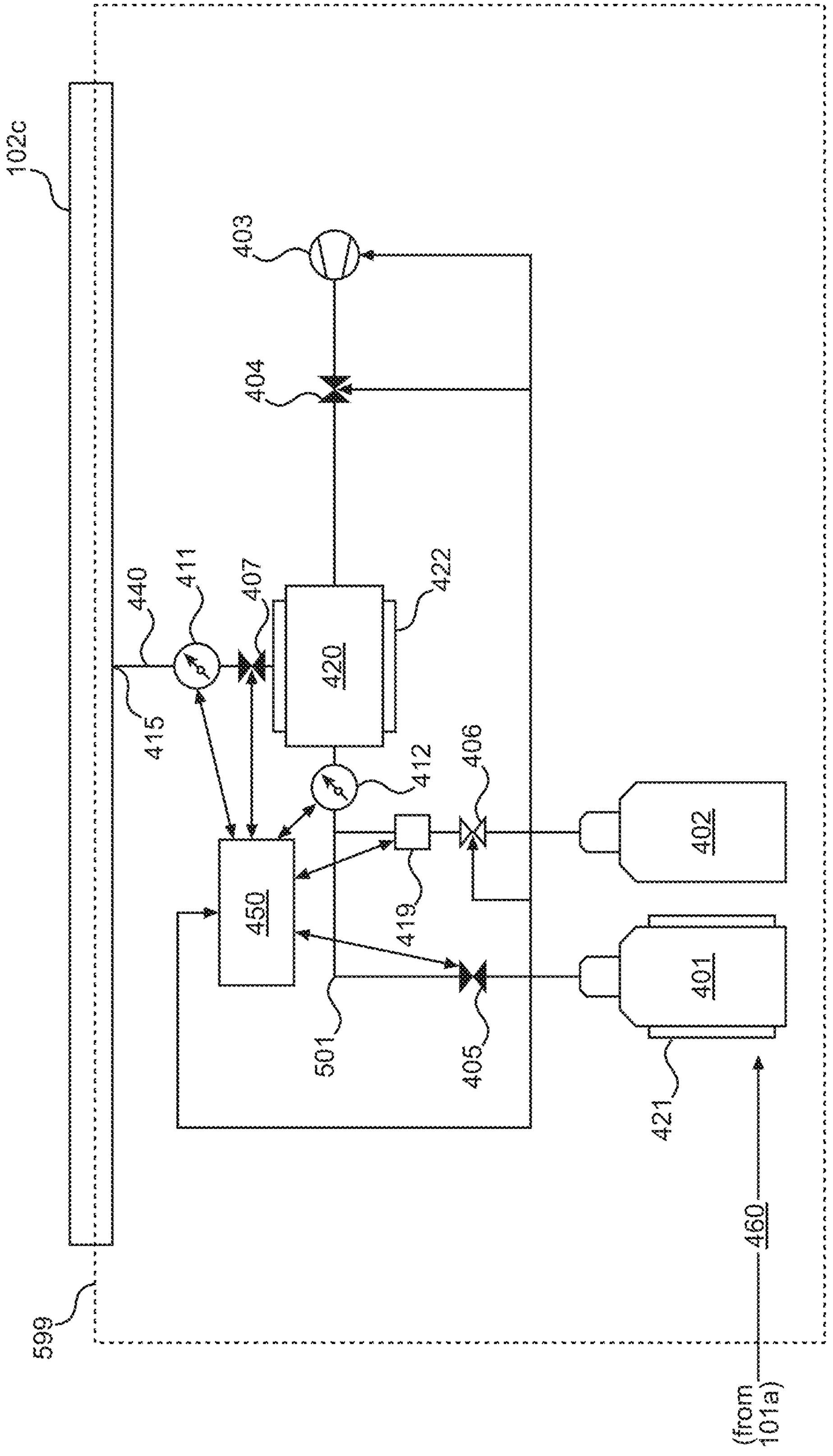

Referring to FIG. 5F, the third valve 406 may be turned or switched on to introduce a carrier gas from the second bottle 402 into the reservoir 420. In at least some example embodiments, the carrier gas from the second bottle 402 may be introduced before, after, concurrently, or alternatively with introduction of NOVEC™ 4710 and/or NOVEC™ 5110 into the reservoir 420.

Figure 5G:
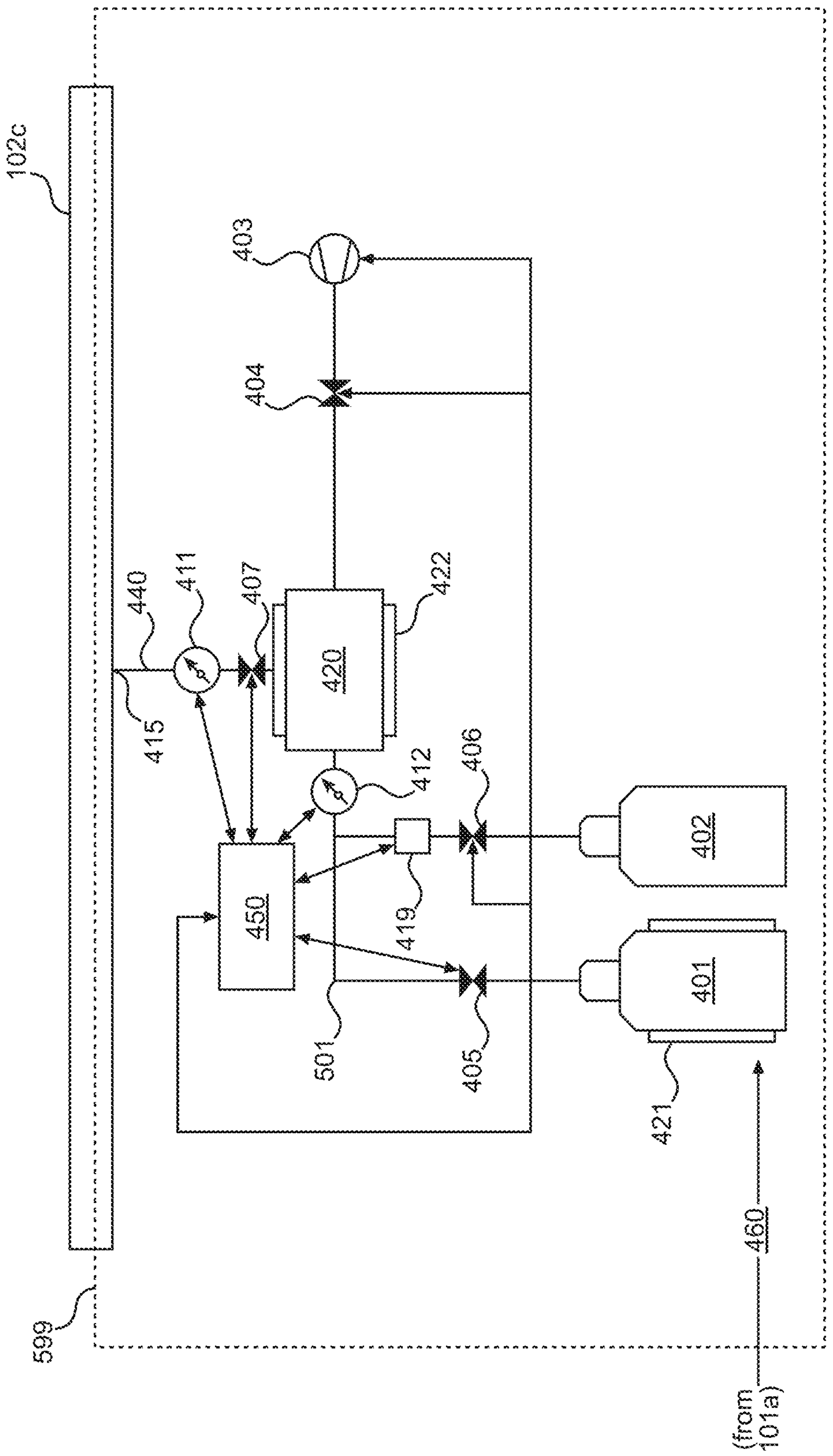

Referring to FIG. 5G, the third valve 406 may be closed or switched off, for example, when a reading in the second gauge 412 indicates a particular pressure within the reservoir 420. The particular pressure may be determined based on a volume of the reservoir 420 and on a desired pressure within the waveguide portion 102*c*.

Figure 5H:
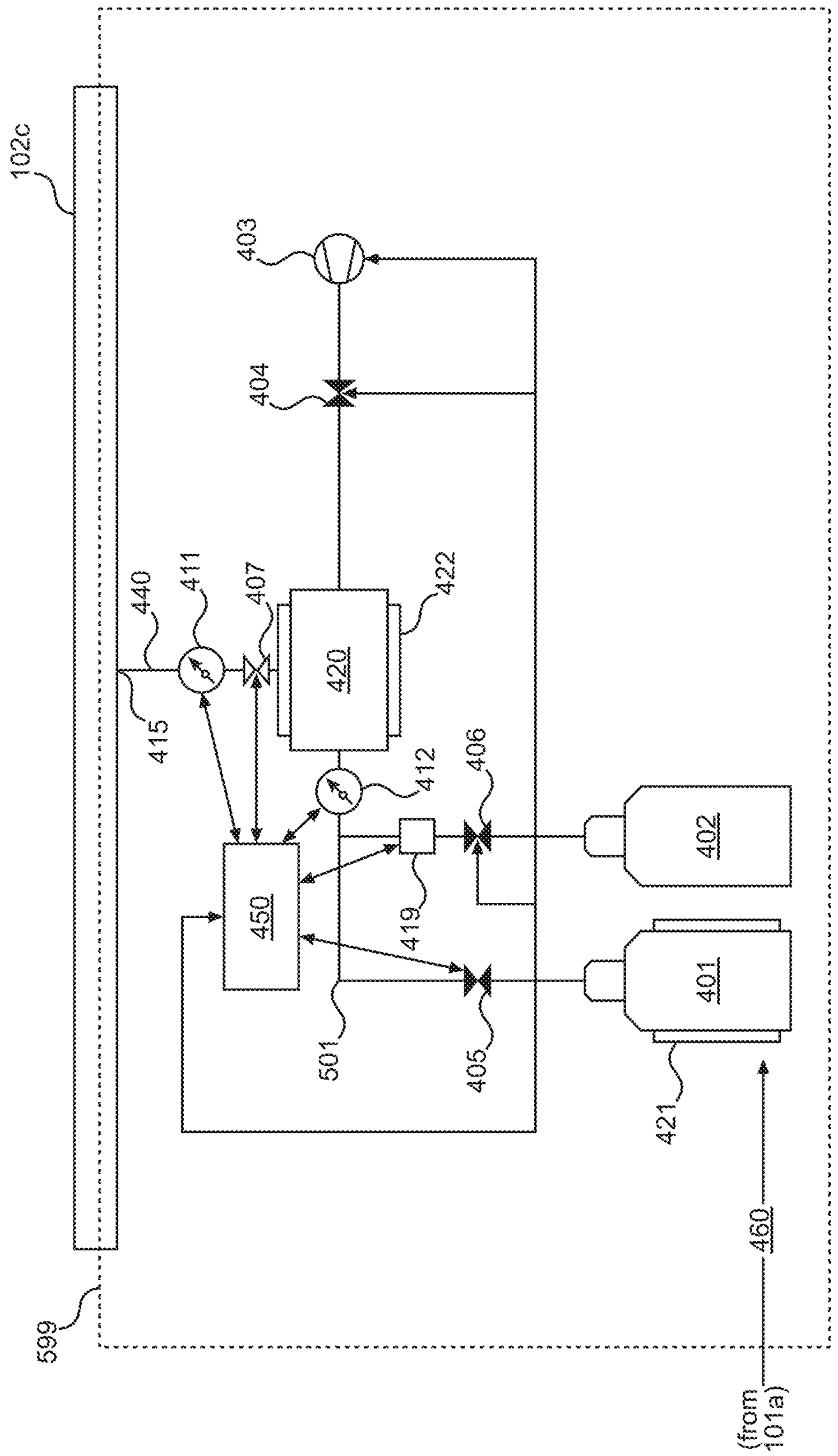

Referring to FIG. 5H, the fourth valve 407 may be turned or switched on to introduce a mixture of NOVEC™ 4710 and/or NOVEC™ 5110 along with the carrier gas into the waveguide portion 102*c*. In at least some example embodiments, the fourth valve 407 may be controlled, for example, by the second gauge 411 via the controller 450.

FIGS. 6A-6H illustrate the mixing cart 699 and a method of introducing gases to a portion of a waveguide, according to various example embodiments. For brevity of explanation, descriptions of like components relative to other examples are omitted. The controller 450 may control and/or communicate with any or all of the various components of the mixing cart 699 shown in FIGS. 5A-5H in the same or substantially the same manner as discussed above with regard to FIGS. 4A-4H.

Referring to FIGS. 6A-6H, the mixing cart 699 may include a scale such as a refrigerant scale 423. The reservoir 420 may sit on the refrigerant scale 423. The refrigerant scale 423 may measure a weight of the reservoir 420, and may determine a volume and/or an amount of gas within the reservoir 420. The amount of gas within the reservoir 420 may be determined based on a tare or unladen weight of the reservoir 420, a volume of the reservoir 420, a molecular mass of either or both of NOVEC™ 4710 or NOVEC™ 5110, a molecular mass of the carrier gas such as carbon dioxide and/or nitrogen, a temperature of gases in the reservoir 420, and a pressure of the reservoir 420. In at least some example embodiments, the temperature, pressure, and volume of gases within the reservoir 420 may obey or be based on the ideal gas law; however, example embodiments are not limited thereto.

Figure 6A:
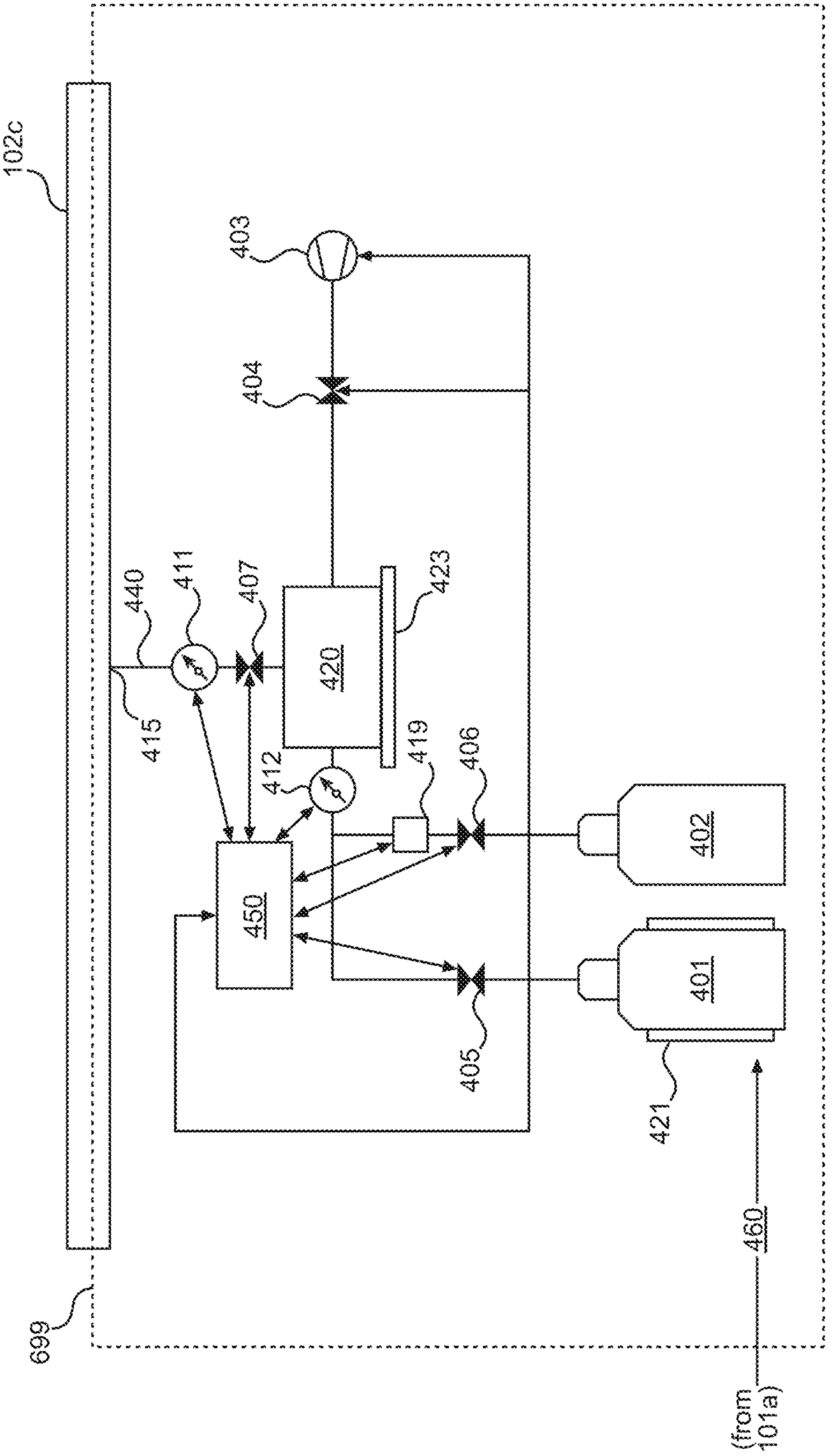
FIGS. 6A-6H illustrate a mixing cart and a method of introducing gases to a portion of a waveguide, according to various example embodiments.

Referring to FIG. 6A, initially the first through fourth valves 404 to 407 may be closed.

Figure 6B:
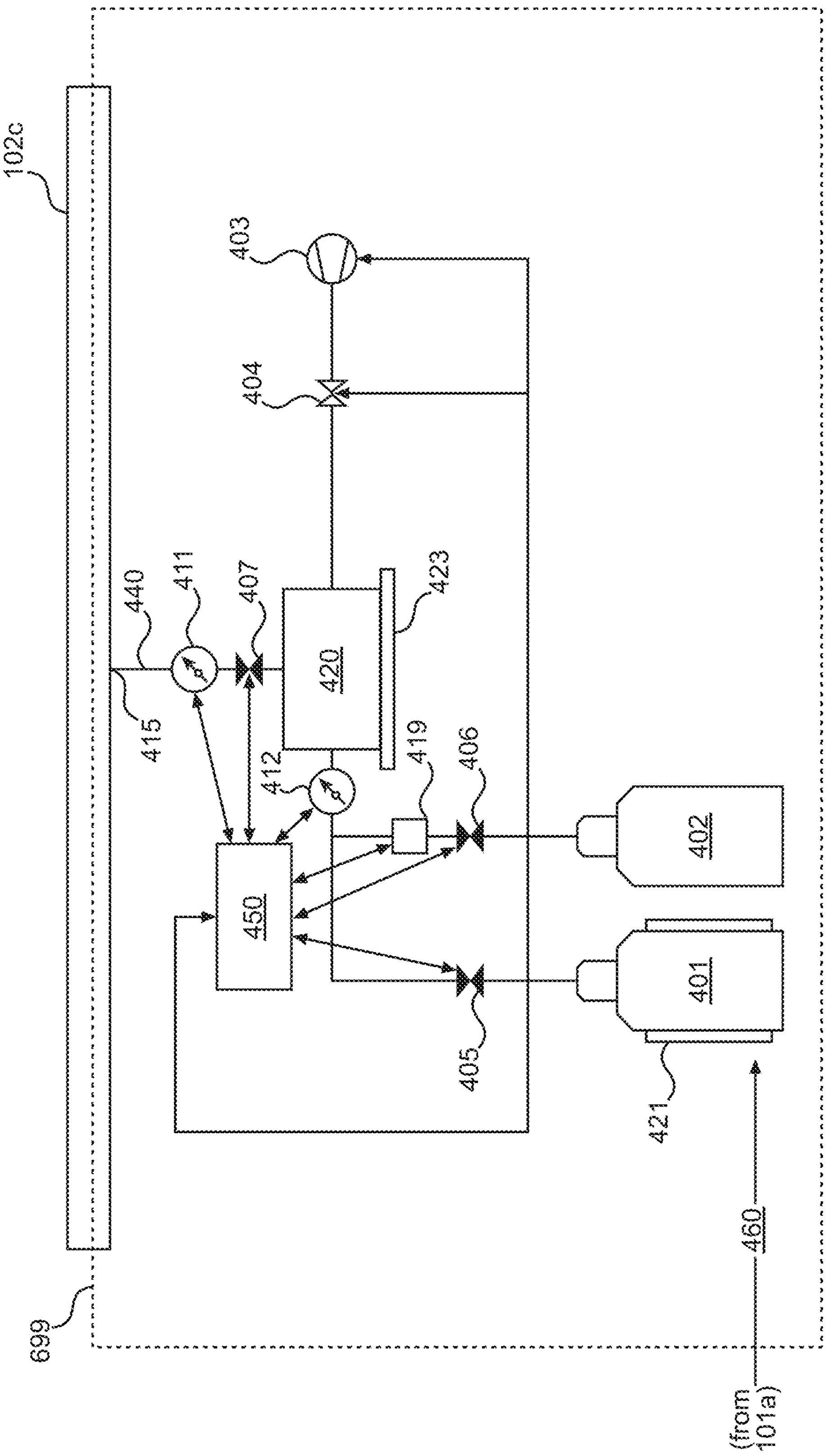

Referring to FIG. 6B, the first valve 404 may be opened or switched on, and the vacuum 403 may be enabled, to evacuate the reservoir 420 to a particular pressure. The particular pressure may be measured with the gauge 412.

Figure 6C:
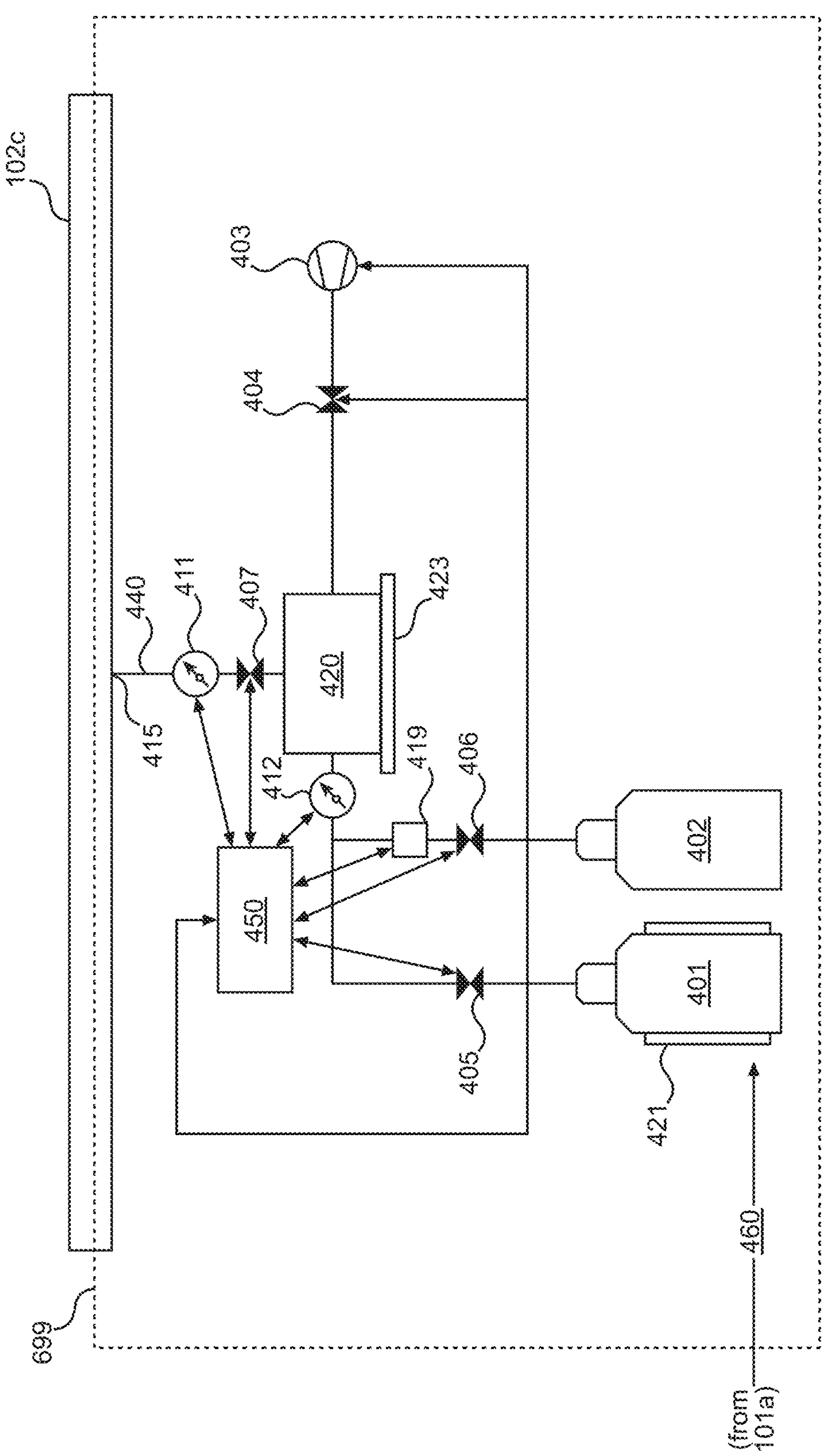

Referring to FIG. 6C, when a pressure in the reservoir 420 is at the particular pressure, the first valve 404 may be closed or turned or switched off. Before, after, or concurrently with the switching off of the first valve 404, the vacuum 403 may be deactivated.

Figure 6D:
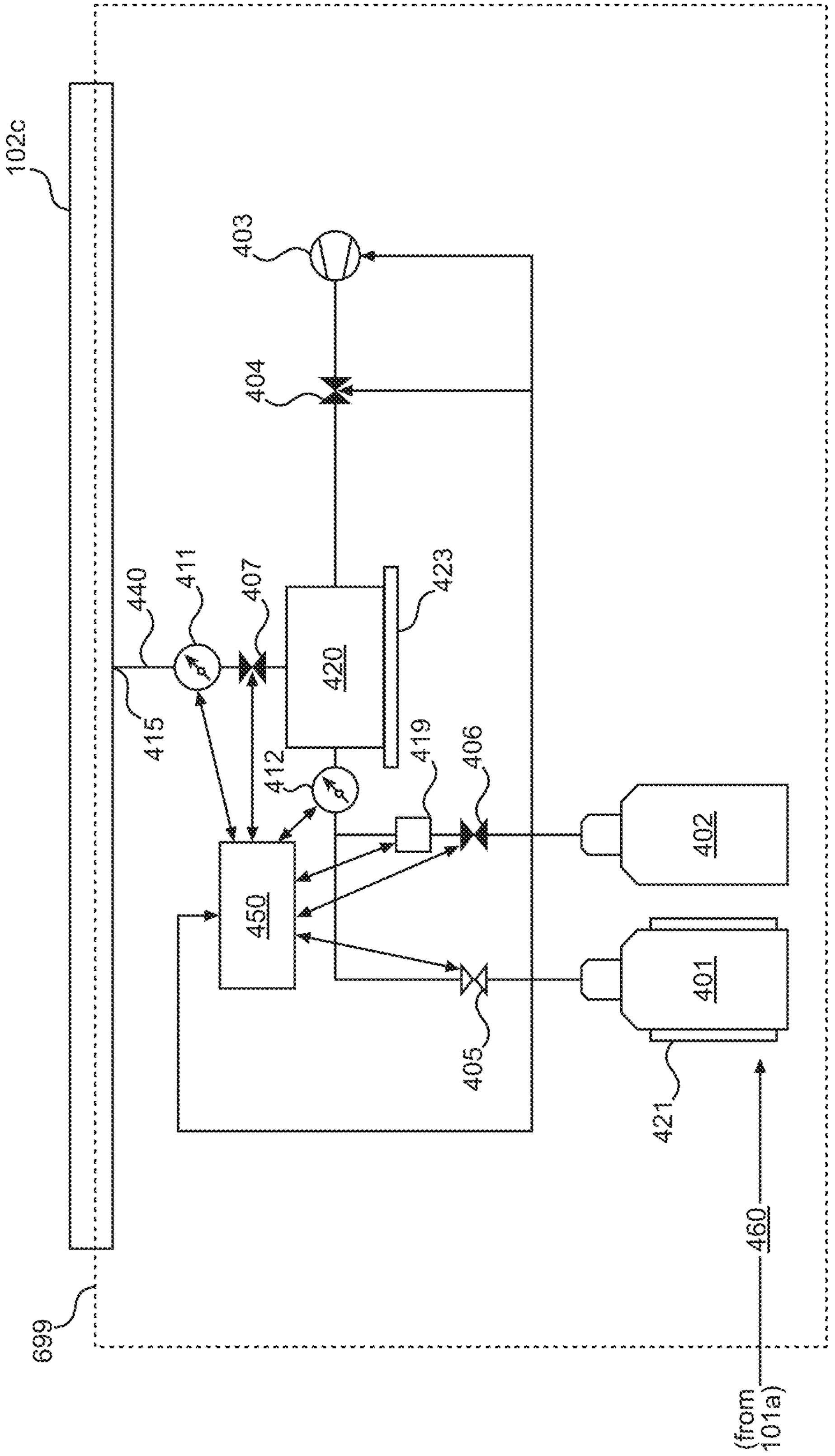

Referring to FIG. 6D, the second valve 405 may be switched on to introduce either or both NOVEC™ 4710 or NOVEC™ 5110 into the reservoir 420. A pressure in the reservoir 420 may be measured, and an amount of mass transfer to the reservoir 420 may be measured by a weight of the refrigerant scale 423.

Figure 6E:
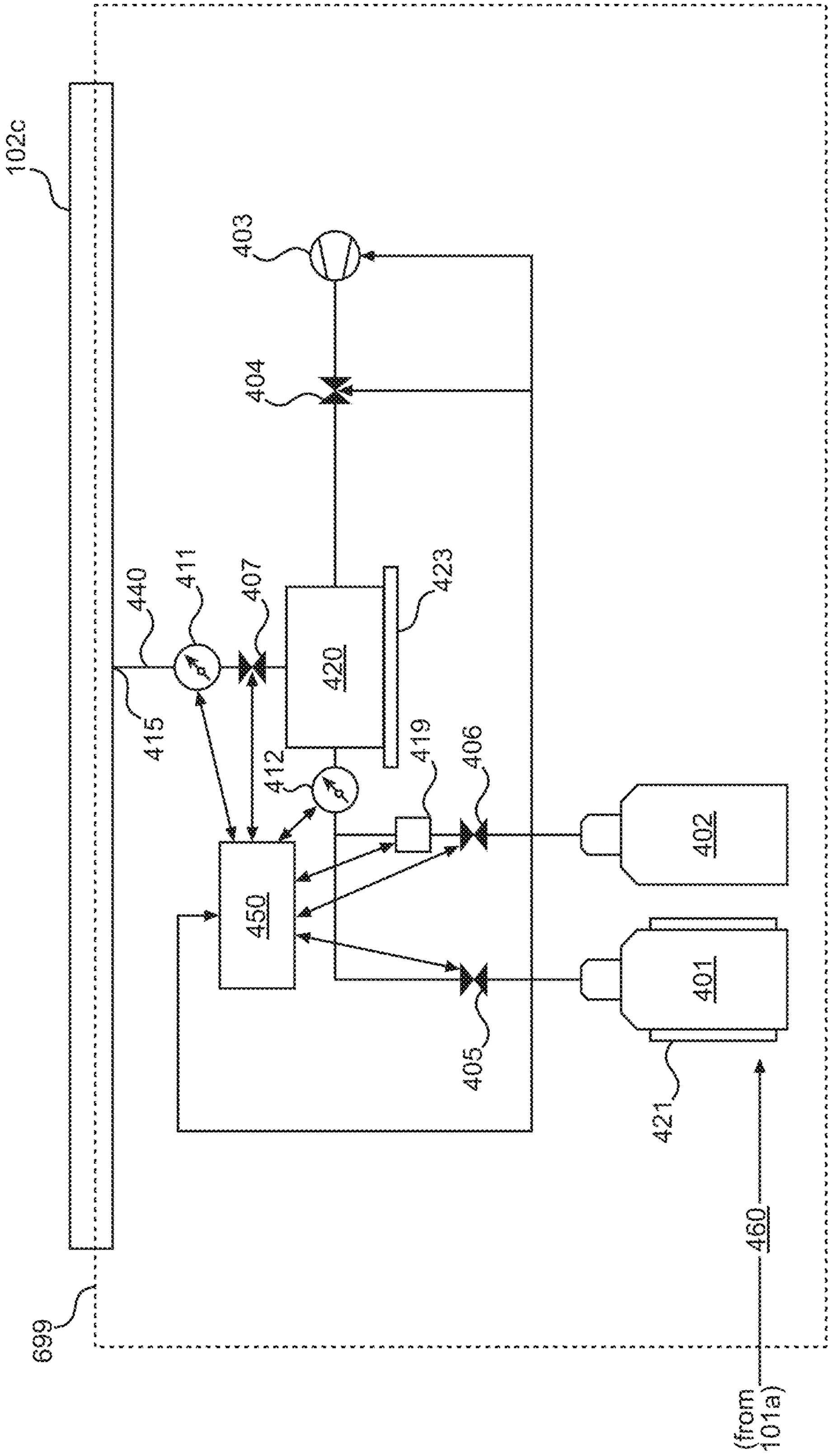

Referring to FIG. 6E, the second valve 405 may be closed or switched off, for example, when a measurement of the refrigerant scale 423 corresponds to a particular weight. The particular weight may be based on a molecular weight of NOVEC™ 4710 and/or NOVEC™ 5110.

Figure 6F:
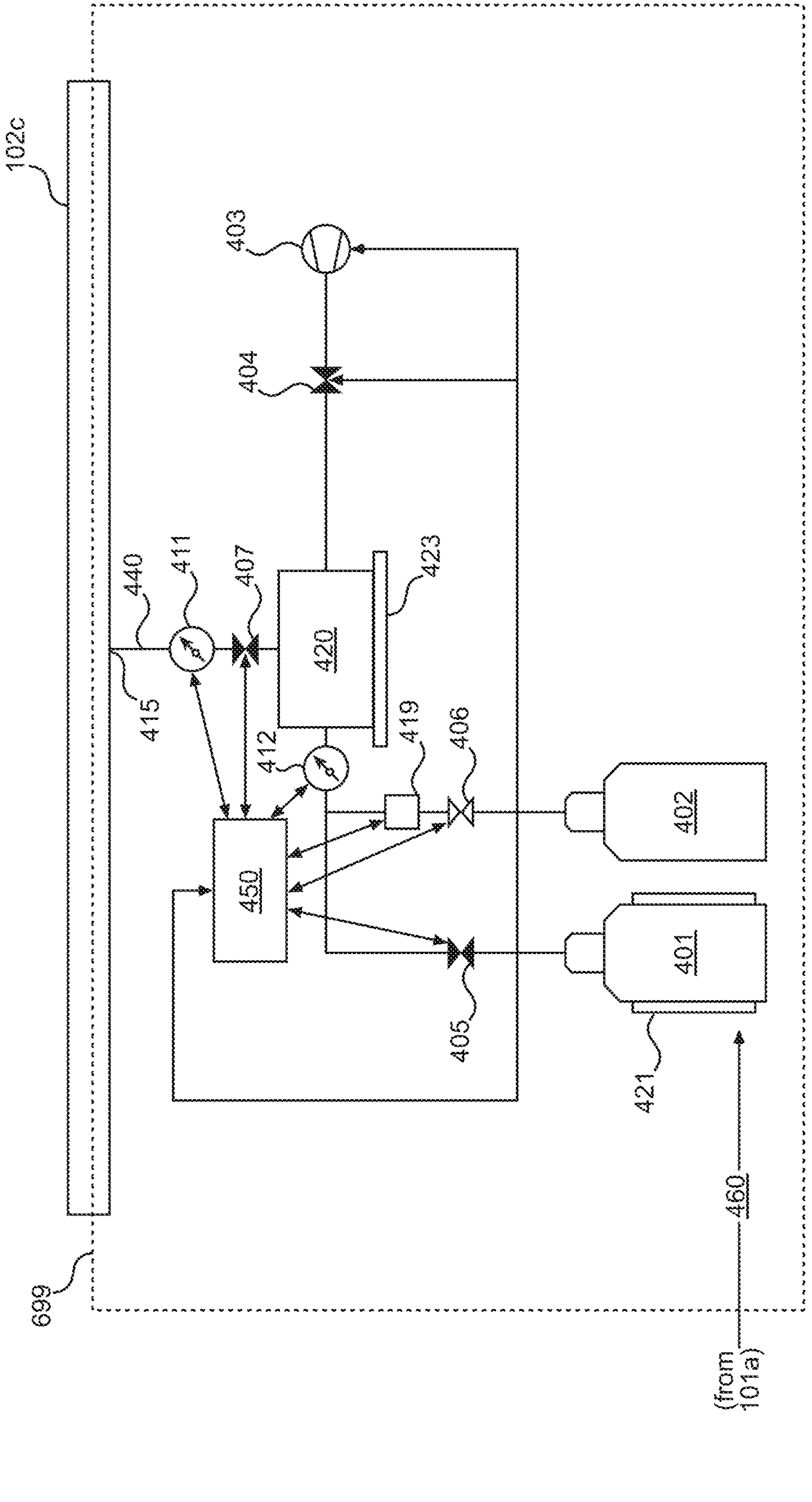

Referring to FIG. 6F, the third valve 406 may be opened or switched on to introduce a carrier gas such as either or both of carbon dioxide and nitrogen into the reservoir 420. In at least some example embodiments, the carrier gas from the second bottle 402 may be introduced to the reservoir 420 before, after, concurrently, or alternatively with the introduction of either or both of NOVEC™ 4710 or NOVEC™ 5110 into the reservoir 420.

Figure 6G:
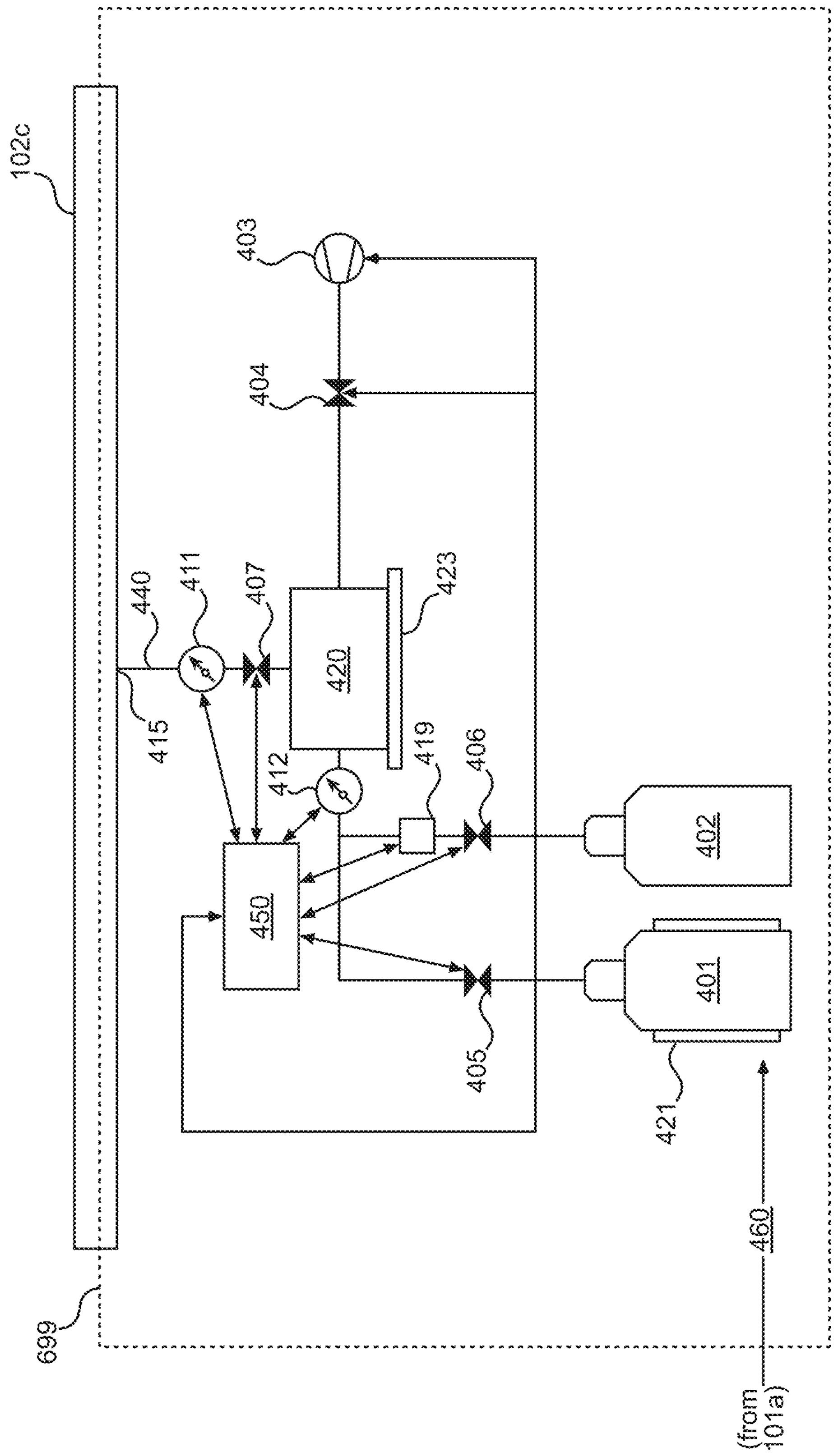

Referring to FIG. 6G, the third valve 406 may be closed or switched off when a reading on the refrigerant scale 423 indicates that an amount of a mixture of the carrier gas and either or both of NOVEC™ 4710 or NOVEC™ 5110 is at a particular value. The particular value may be based on a pressure of the mixture to be introduced to the waveguide portion 102*c*.

Figure 6H:
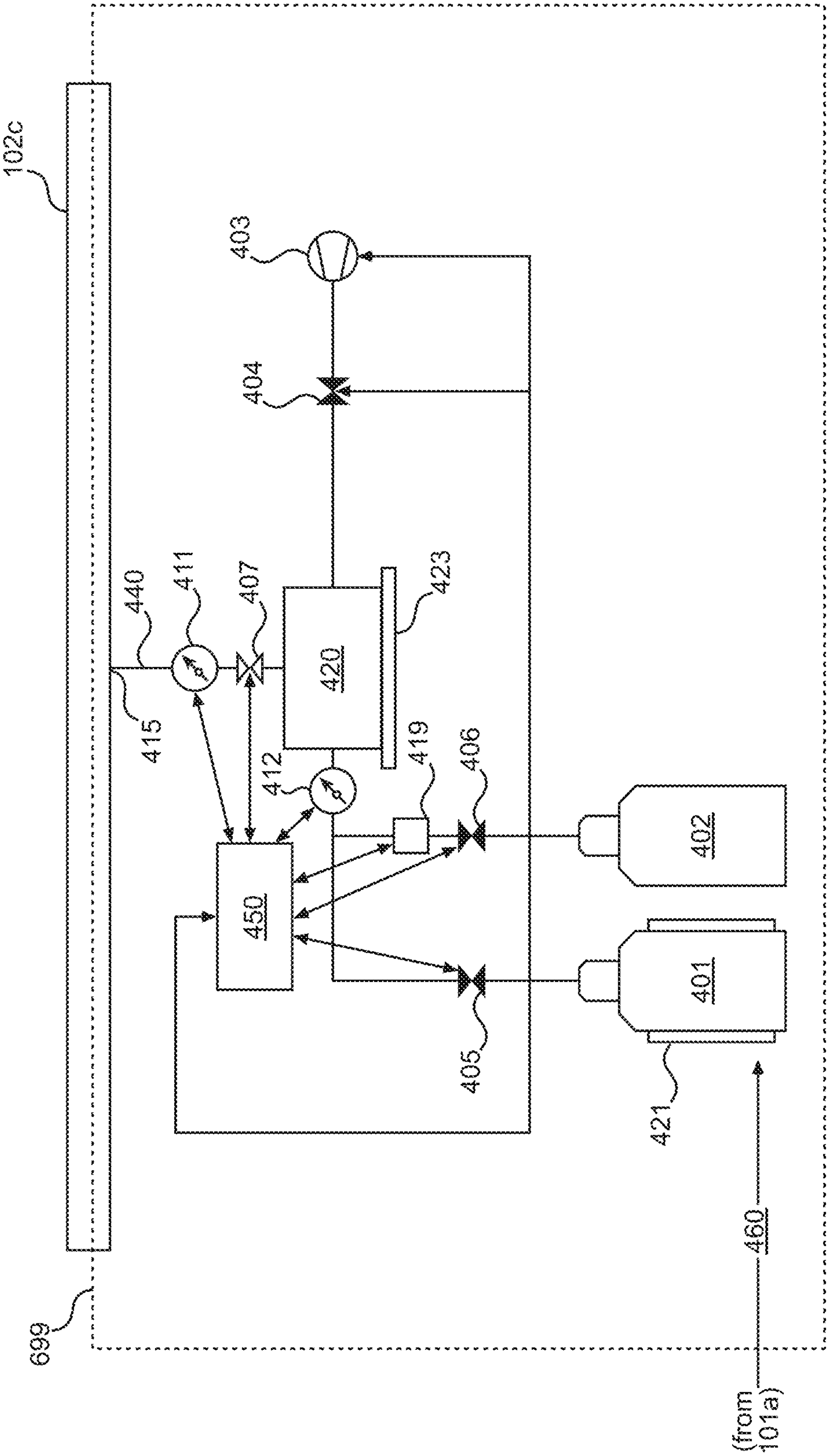

Referring to FIG. 6H, the fourth valve 407 may be open or switched on, and the mixture from the reservoir 420 may be introduced into the waveguide portion 102*c*. A pressure reading of the first gauge 411 may control and actuate the fourth valve 407; however, example embodiments are not limited thereto.

Figure 7:
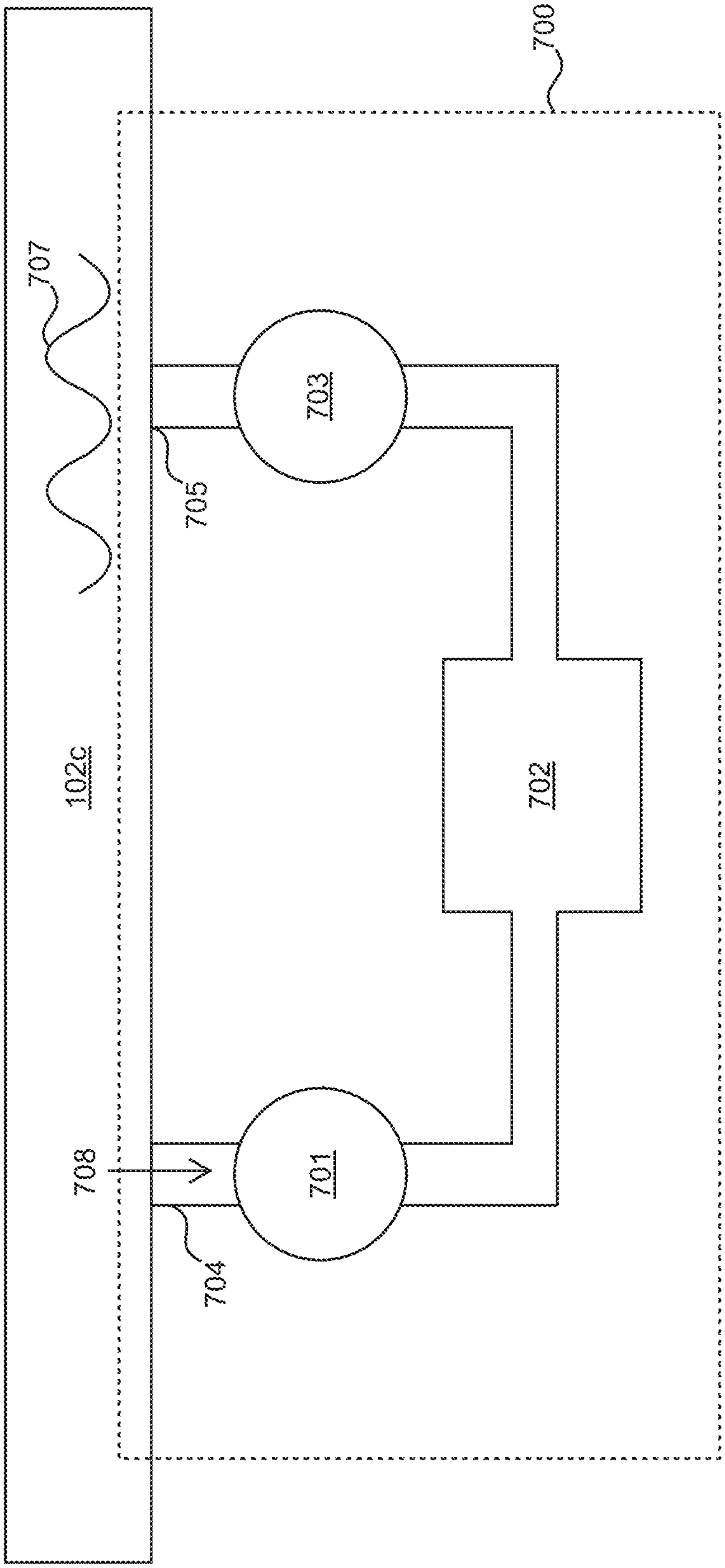
FIGS. 7 and 8 illustrate a portion of a waveguide along with a gas management system, according to various example embodiments.
Figure 8:
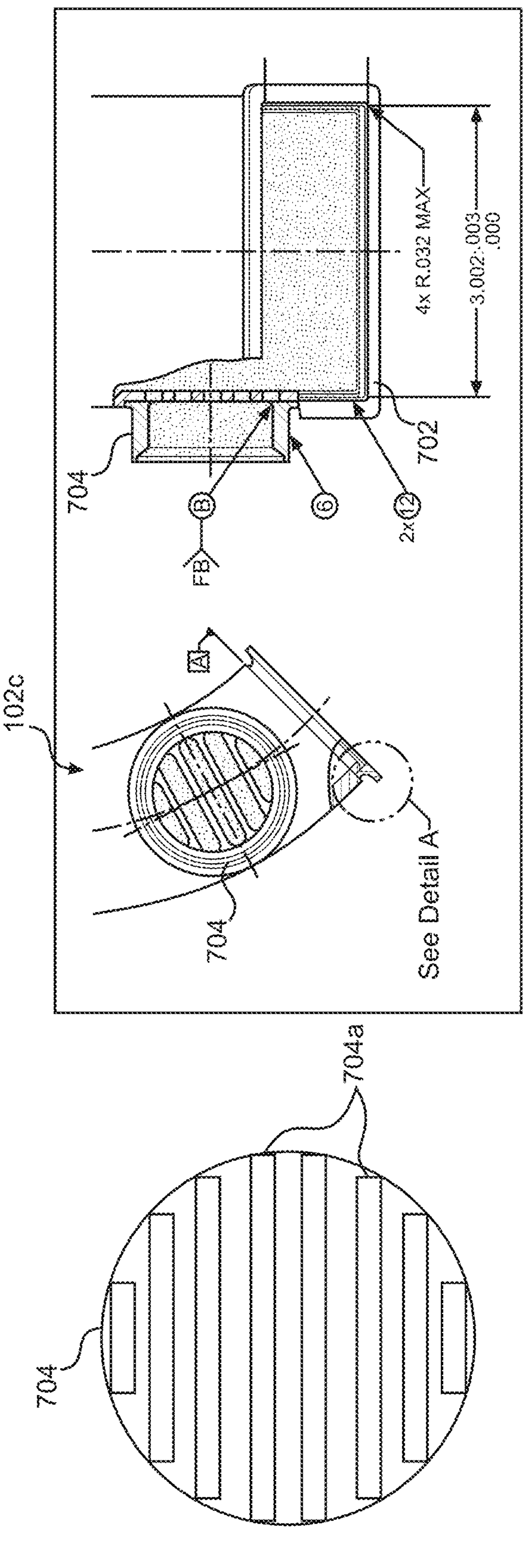

FIG. 7 illustrates a portion of a waveguide along with a gas management system, according to various example embodiments. FIG. 8 illustrates an aperture according to various example embodiments. Example embodiments are described with reference to the third waveguide portion 102*c* for brevity; however, example embodiments are not limited to this example.

Referring to FIGS. 7 and 8, a gas management system 700 may include a fifth valve 701, a sixth valve 703, and a gas management device 702. The gas management system 700 may be connected to, and/or in fluid communication with the third waveguide portion 102*c*. An RF wave 707 may propagate a length of the waveguide portion 102*c*. There may be one or more interfaces, such as first and second RF-blocking apertures 704 and 705, along a length of the waveguide portion 102*c*.

Either or both of the first and second RF-blocking apertures 704 and 705 may at least partially block RF waves, for example the RF wave 707, from leaving the third waveguide portion 102*c* and extending into the gas management system 700, while enabling gas, such as gas 708, to enter to the gas management system 700. The gas 708 may be one or more of NOVEC™ 4710, NOVEC™ 5110, and/or a carrier gas such as carbon dioxide and/or nitrogen.

Either or both of the first and second RF-blocking apertures 704 and 705 may have a plurality of openings, such as a plurality of slits 704*a*. The plurality of slits 704*a* may be or include gratings and/or vents, and may be or correspond to pressure tight aperture adapters. A size of each of the plurality of slits 704*a* may be such that gases such as one or more of NOVEC™ 4710, NOVEC™ 5110, or a carrier gas freely flows into the gas management system 700, and may also be sized such that RF wave 707 is at least partially blocked from entering the gas management system 700.

In at least some example embodiments, valves such as fifth and sixth valves 701 and 703 may be arranged to control the gas 708 entering into and out of the gas management device 702. The gas management device 702 may adsorb and/or agitate gases. In at least some example embodiments, the gas management device 702 may be vestigial or extend as a spur, and may (e.g., may only) be connected to the third waveguide portion 102*c* at one end and through one aperture such as the first RF-blocking aperture 704. Example embodiments are not limited thereto, however, and in some cases the gas management device 702 may be connected to the third waveguide portion 102*c* through two or more apertures such as the first RF-blocking aperture 704 and the second RF-blocking aperture 705.

Gases such as NOVEC™ 4710 or NOVEC™ 5110 are at least slightly polar molecules. This is in contrast to gases such as $SF_6$. Accordingly, molecules such as NOVEC™ 4710 or NOVEC™ 5110 may rotate somewhat in response to radiofrequency electromagnetic radiation. Accordingly the gases such as NOVEC™ 4710 or NOVEC™ 5110 may be hotter during use than that of $SF_6$. There may be noise or audible vibration.

In at least some example embodiments, the gas management device 702 may be or may include one or more of a desiccant to help maintain dryness in the radiation therapy machine 100, a cooling mechanism such as a fan and/or other agitator, an electric heating element for convection. In at least one example, the desiccant may be balls of silica or more specialized similar porous materials designed specifically for industrial applications.

In at least some example embodiments, the gas management device 702 may help reduce breakdown of byproducts included in the gas management device 702. In at least some example embodiments, the gas management device 702 may help to mitigate one or more of the temperature variation, the dryness, the breakdown of byproducts, or the vibrations of gases such as NOVEC™ 4710 or NOVEC™ 5110.

Figure 9:
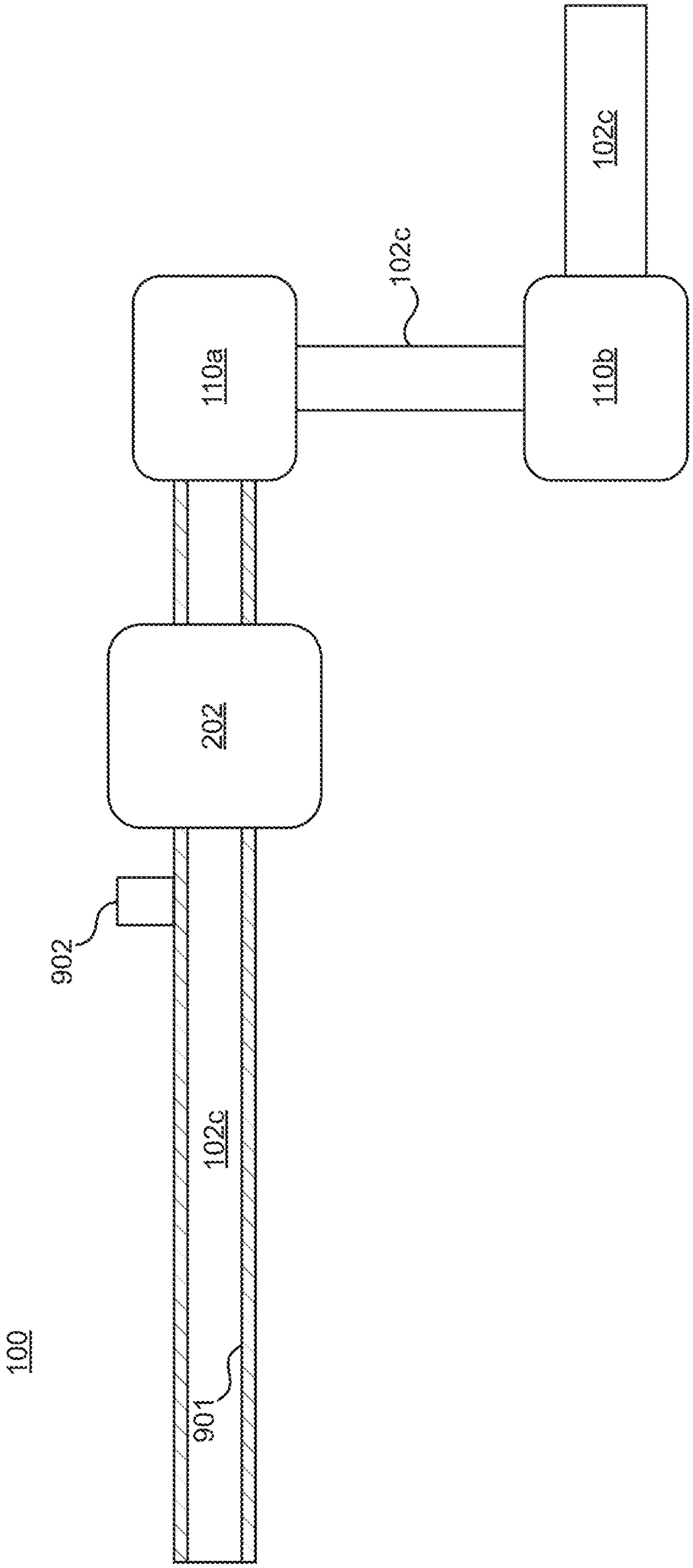
FIG. 9 illustrates a portion of a waveguide, according to various example embodiments.

FIG. 9 is an illustration of a portion of a radiation therapy machine, according to various example embodiments.

Referring to FIG. 9, gases such as NOVEC™ 5110 within a radiation therapy machine 100 may be particularly susceptible to ultraviolet degradation. For example, gases such as NOVEC™ 5110 may be designed to break down in the upper atmosphere of the earth, so as to reduce global warming potential.

However, events such as arcing within a radiation therapy machine 100 may generate ultraviolet radiation. An excessive amount of arcing events may ultimately break down much or all of the gases such as NOVEC™ 5110.

According to various example embodiments, a waveguide portion such as the third waveguide portion 102*c* in FIG. 9 may include an ultraviolet mitigation component such as a coating 901 on an inner wall thereof. The coating 901 may be a coating 901 on an inside an inner wall of the waveguide portion 102*c*. The coating 901 may mitigate or reduce ultraviolet degradation. In at least some example embodiments, an inner wall of the waveguide portion 102*c* may be lined with the coating 901, which may wholly or at least partially absorb radiation such as ultraviolet radiation, that may be generated by arcing events within the waveguide portion 102*c*.

In at least some example embodiments, the coating 901 may be a paint such as a black paint, and/or may be pitted, so as to absorb ultraviolet radiation. The coating 901 may be or may include an antireflective coating that is sensitive to ultraviolet radiation such as ultraviolet radiation that causes breakdown of gases such as NOVEC™ 5110, and that otherwise does not add or minimally affects dielectric and/or resistive loss.

Alternatively, or additionally, the coating 901 may have dielectric properties to prevent, mitigate, or reduce an amount of breakdown of gases such as NOVEC™ 5110.

Alternatively, or additionally, the radiation therapy machine 100 may include arc detection sensors such as optical arc detection sensors 902, that may be attached to and/or inside of waveguide portions such as waveguide portion 102*c*. The optical arc detection sensors 902 may generate alarms and/or alerts based on an amount of and/or a frequency of arc events, which may indicate an excessive amount of ultraviolet radiation which may be detrimental to the gases such as NOVEC™ 5110.

Alternatively, or additionally, the radiation therapy machine 100 may include particular bends such as electric/magnetic (E/H) bends 110*a* and 110*b*. These E/H bends may be located to wholly or at least partially break up a line of sight within waveguide portions such as waveguide portion 102*c*.

Various example embodiments describe radiation therapy machines and/or portions of radiation therapy machines that may use a gas such as NOVEC™ 4710 or NOVEC™ 5110 as a dielectric gas within waveguides, in addition to or in lieu of $SF_6$. Alternatively, or additionally, various example embodiments describe methods of filling radiation therapy machines with gases such as NOVEC™ 4710 or NOVEC™ 5110. Alternatively, or additionally, various example embodiments describe waveguide portions and improvements to waveguides that help mitigate deleterious effects from gases such as NOVEC™ 4710 or NOVEC™ 5110.

Any of the elements and/or functional blocks disclosed above may include or be implemented in processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processing circuitry may include electrical components such as at least one of transistors, resistors, capacitors, etc. The processing circuitry may include electrical components such as logic gates including at least one of AND gates, OR gates, NAND gates, NOT gates, etc.

When the terms "about" or "substantially" are used in this specification in connection with a numerical value, it is intended that the associated numerical value includes a manufacturing or operational tolerance (e.g., ±10%) around the stated numerical value. Moreover, when the words "generally" and "substantially" are used in connection with geometric shapes, it is intended that precision of the geometric shape is not required but that latitude for the shape is within the scope of the disclosure. Moreover, when the words "generally" and "substantially" are used in connection with material composition, it is intended that exactitude of the material is not required but that latitude for the material is within the scope of the disclosure.

Further, regardless of whether numerical values or shapes are modified as "about" or "substantially," it will be understood that these values and shapes should be construed as including a manufacturing or operational tolerance (e.g., ±10%) around the stated numerical values or shapes. Thus, while the term "same," "identical," or "equal" is used in description of example embodiments, it should be understood that some imprecisions may exist. Thus, when one element or one numerical value is referred to as being the same as another element or equal to another numerical value, it should be understood that an element or a numerical value is the same as another element or another numerical value within a desired manufacturing or operational tolerance range (e.g., ±10%).

Various example embodiments being thus described, it will be obvious that the same may be varied in many ways. Such variations are not to be regarded as a departure from the spirit and scope of example embodiments, and all such modifications as would be obvious to one of ordinary skill in the art are intended to be included within the scope of the claims. Example embodiments are further not necessarily mutually exclusive with one another. For example, some example embodiments may include one or more features described with reference to one or more drawings, and may also include one or more other features described with reference to one or more other drawings.

What is claimed is:

1. A microwave network for a radiation therapy machine having a microwave source and a linear accelerator, the microwave network comprising:

a waveguide configured to connect between the microwave source and the linear accelerator, a first portion of the waveguide containing at least one of a first gas or a second gas having a first characteristic, the first gas being 2,3,3,3-tetrafluoro-2-(trifluoromethyl) propanenitrile and the second gas being 1,1,1,3,4,4,4-heptafluoro-3-(trifluoromethyl)-2-butanone, and a second portion of the waveguide containing at least one of the first gas or the second gas having a second characteristic, the second characteristic being different from the first characteristic; and a gas management device configured to adjust the first characteristic or the second characteristic of the at least one of the first gas or the second gas in the first portion and the second portion.

2. The microwave network of claim 1, wherein the first portion of the waveguide includes the first gas and a carrier gas, and a molar percentage of the carrier gas in the first portion of the waveguide is between about 60% and about 90%.

3. The microwave network of claim 2, wherein the carrier gas is carbon dioxide, the molar percentage of the first gas within the first portion of the waveguide is between about 13.5% and about 16.5%, and a total pressure in the first portion of the waveguide is between about 27.5 pound force per square inch gauge (psig) and about 32.5 psig.

4. The microwave network of claim 1, wherein a total pressure of the first portion of the waveguide containing at least one of the first gas or the second gas is less than about 90 psig.

5. The microwave network of claim 1, at least a portion of the waveguide includes an ultraviolet mitigation component.

6. The microwave network of claim 5, wherein the ultraviolet mitigation component includes a coating on an inner wall of the portion, the coating being antireflective with respect to ultraviolet radiation.

7. The microwave network of claim 6, wherein the coating is a dielectric.

8. A mass-flow mixing cart to supply gases to a waveguide for a radiation therapy system, the mass-flow mixing cart comprising:

a vacuum pump;

a first valve connected to the vacuum pump, the first valve configured to control a vacuum pressure of at least a portion of the waveguide;

a second valve configured to control introduction of a first gas into the portion of the waveguide, the first gas being one of 2,3,3,3-tetrafluoro-2-(trifluoromethyl) propanenitrile or 1,1,1,3,4,4,4-heptafluoro-3-(trifluoromethyl)-2-butanone; and a third valve configured to control an introduction of a second gas into the portion of the waveguide, the second gas being a carrier gas.

9. The mass-flow mixing cart of claim 8, further comprising:

a first mass flow meter connected to the first valve, the first mass flow meter configured to measure a flowrate of the first gas; and a second mass flow meter connected to the second valve, the second mass flow meter configured to measure a flowrate of the second gas.

10. The mass-flow mixing cart of claim 8, further comprising:

a first gauge configured to measure a pressure of the portion of the waveguide.

11. The mass-flow mixing cart of claim 10, further comprising:

a reservoir connected to the first valve and to the second valve, the reservoir configured to store a mixture of the first gas and the second gas.

12. The mass-flow mixing cart of claim 11, further comprising:

a reservoir heater at least partially surrounding the reservoir, and configured to heat the reservoir.

13. The mass-flow mixing cart of claim 11, further comprising:

a refrigerant scale configured to hold the reservoir.

14. A method of supplying a gas to a portion of a waveguide for a radiation therapy machine, the method comprising:

heating a bottle with water from a water supply of the radiation therapy machine, the bottle including a first gas;

supplying the first gas from the bottle to a piping that is in fluid communication with the portion of the waveguide, the first gas being one of 2,3,3,3-tetrafluoro-2-(trifluoromethyl) propanenitrile or 1,1,1,3,4,4,4-heptafluoro-3-(trifluoromethyl)-2-butanone; and supplying a carrier gas to the piping.

15. The method of claim 14, further comprising:

supplying the first gas into a reservoir;

supplying the carrier gas into the reservoir until at least one of a total weight of the reservoir reaches a threshold weight or a total pressure of the reservoir reaches a threshold pressure; and supplying a mixture of the first gas and the carrier gas from the reservoir into the portion of the waveguide.

16. A gas management system for a microwave network including a waveguide, the gas management system comprising:

a gas management device configured to adjust a characteristic of a gas in the waveguide; and a first radiofrequency (RF)-blocking interface in fluid communication with the waveguide and with the gas management device, the first RF-blocking interface defining a plurality of vents, the plurality of vents configured to suppress radiofrequency wave from flowing into the gas management device and configured to allow the gas to enter the gas management device.

17. The gas management system of claim 16, wherein the gas management device is configured to adjust at least one of a dryness of the gas or a breakdown of byproducts in the gas.

18. The microwave network of claim 1, wherein the first characteristic of the at least one of the first gas or the second gas in the first portion of the waveguide includes at least one of:

pressure;

temperature;

dryness; or a breakdown of byproducts in the first gas or the second gas.

* * * * *